US012773497B2

(12) United States Patent
Kim

(10) Patent No.: US 12,773,497 B2
(45) Date of Patent: Oct. 27, 2026

(54) METHOD, DEVICE, AND COMPUTER PROGRAM PRODUCT FOR DETERMINING OCCURRENCE OF INLET OCCLUSION OF DRUG INJECTION DEVICE

(71) Applicant: INSULET CORPORATION, Acton, MA (US)

(72) Inventor: Seonhwan Kim, Seongnam-si (KR)

(73) Assignee: INSULET CORPORATION, Acton, MA (US)

( * ) Notice: Subject to any disclaimer, the term of this patent is extended or adjusted under 35 U.S.C. 154(b) by 823 days.

(21) Appl. No.: 18/118,967

(22) Filed: Mar. 8, 2023

(65) Prior Publication Data

US 2023/0248902 A1 Aug. 10, 2023

Related U.S. Application Data

(63) Continuation of application No. PCT/KR2021/008628, filed on Jul. 7, 2021.

(30) Foreign Application Priority Data

Sep. 10, 2020 (KR) ........................ 10-2020-0116213

(51) Int. Cl.
*A61M 5/168* (2006.01)
*A61M 5/142* (2006.01)

(52) U.S. Cl.
CPC ................... *A61M 5/16831* (2013.01); *A61M 2005/14208* (2013.01); *A61M 5/14216* (2013.01); *A61M 2005/16863* (2013.01)

(58) Field of Classification Search
CPC .... A61M 2005/14208; A61M 5/14212; A61M 5/14216; A61M 5/1422; A61M 5/16831; A61M 2005/16863; A61M 2005/16868; A61M 2005/16872; A61M 2205/106;
(Continued)

(56) References Cited

U.S. PATENT DOCUMENTS 5,217,355 A 6/1993 Hyman et al.
5,647,853 A 7/1997 Feldmann et al.
(Continued)

FOREIGN PATENT DOCUMENTS

JP 2007533381 A 11/2007
JP 2018518320 A 7/2018
(Continued)

*Primary Examiner* — Kami A Bosworth
*Assistant Examiner* — Avery Smale
(74) *Attorney, Agent, or Firm* — Goodwin Procter LLP

(57) ABSTRACT

A medical liquid injection device may include a pump module, a pivot fitting, at least one sensor, and a processor. The pump module may include a shaft configured to perform a linear reciprocating movement along one direction. The pivot fitting may include a first end connected to the shaft and a second end configured to perform a rotational reciprocating movement by the linear reciprocating movement. The at least one sensor may obtain contact time information on a time at which at least one sensor comes into contact with the second end. The processor may calculate a driving time of the pump module using the contact time information and determine occurrence of occlusion of the medical liquid injection device on the basis of the driving time.

8 Claims, 18 Drawing Sheets

(58) Field of Classification Search
CPC ...... A61M 2205/3368; A61M 5/14248; A61M 2005/14264
See application file for complete search history.

(56) References Cited

U.S. PATENT DOCUMENTS

| | | | | |
|---|---|---|---|---|
| 2007/0083292 | A1* | 4/2007 | Knauper | A61M 5/16831 700/282 |
| 2014/0155867 | A1* | 6/2014 | Lee | G01F 1/6847 73/204.22 |
| 2016/0367754 | A1* | 12/2016 | Alderete, Jr. | F04B 7/04 |

FOREIGN PATENT DOCUMENTS

| | | | |
|---|---|---|---|
| WO | 2008067314 | A1 | 6/2008 |
| WO | 2016209554 | A1 | 12/2016 |

* cited by examiner

METHOD, DEVICE, AND COMPUTER PROGRAM PRODUCT FOR DETERMINING OCCURRENCE OF INLET OCCLUSION OF DRUG INJECTION DEVICE

CROSS-REFERENCE TO RELATED APPLICATIONS

This application is a continuation of PCT/KR2021/008628 filed on Jul. 7, 2021, which claims priority to Korean Patent Application No. 10-2020-0116213 filed on Sep. 10, 2020, entire contents of which are herein incorporated by reference.

TECHNICAL FIELD

The present disclosure provides a method, a device, and a computer program product for determining the occurrence of inlet occlusion of a medical liquid injection device.

BACKGROUND ART

Diabetes is a metabolic disorder that generates a sign indicating that a blood sugar level exceeds a normal range because of insufficient insulin secretion or abnormal function. The diabetes is a complex disease that possibly affects individual tissues of a human body due to complications such as blindness, renal failure, heart failure, and neuropathy, and the like, and the number of diabetic patients is increasing every year.

In the case of diabetes, it is necessary to measure a blood sugar level using a blood sugar meter, and to manage the blood sugar level through appropriate means such as diet, exercise program, insulin injection, oral diabetes medication, and the like.

Recently, there is a need to develop a technology for more accurately determining the occurrence of inlet occlusion of a medical liquid injection device.

SUMMARY

Technical Problem

The present disclosure is directed to providing a method, a device, and a computer program product for determining the occurrence of inlet occlusion of a medical liquid injection device. The technical problem to be achieved by the present embodiment is not limited to the above-described technical problems, and other technical problems may be deduced from the following embodiments.

Technical Solution to Problem

As a technical means for achieving the above-described technical problem, a first aspect of the present disclosure may provide a medical liquid injection device including a pump module including a shaft configured to perform a linear reciprocating movement along one direction, a pivot fitting including a first end connected to the shaft and a second end configured to perform a rotational reciprocating movement by the linear reciprocating movement, at least one sensor configured to obtain contact time information on a time at which the at least one sensor comes into contact with the second end, and a processor configured to calculate a driving time of the pump module using the contact time information, and determine occurrence of inlet occlusion of the medical liquid injection device on the basis of the driving time.

A second aspect of the present disclosure may provide a method of determining occurrence of inlet occlusion of a medical liquid injection device, the method including obtaining contact time information on a time at which at least one sensor comes into contact with a pivot fitting connected to a pump module, calculating a driving time of the pump module using the contact time information, and determining occurrence of inlet occlusion of the medical liquid injection device on the basis of the driving time, wherein the determining of the occurrence of the inlet occlusion of the medical liquid injection device may include calculating a filtering time by filtering a predetermined number of consecutive driving times, calculating an evaluation value by in such a manner that when a difference between a current filtering time and a previous filtering time is greater than or equal to a first reference value, the evaluation value is increased, and when the difference between the current filtering time and the previous filtering time is less than the first reference value, the evaluation value is decreased, and determining that the inlet occlusion of the medical liquid injection device has occurred when the evaluation value is greater than or equal to a second reference value.

A third aspect of the present disclosure may provide a computer program product including one or more computer-readable media storing a program for implementing a method including obtaining contact time information on a time at which at least one sensor comes into contact with a pivot fitting connected to a pump module, calculating a driving time of the pump module using the contact time information, and determining occurrence of inlet occlusion of a medical liquid injection device on the basis of a driving time, wherein the determining of the occurrence of the inlet occlusion of the medical liquid injection device may include calculating a filtering time by filtering a predetermined number of consecutive driving times, calculating an evaluation value in such a manner that when a difference between a current filtering time and a previous filtering time is greater than or equal to a first reference value, the evaluation value is increased, and when the difference between the current filtering time and the previous filtering time is less than the first reference value, the evaluation value is decreased, and determining that the inlet occlusion of the medical liquid injection device has occurred when the evaluation value is greater than or equal to a second reference value.

Advantageous Effects of Disclosure

According to the above-described problem solving means of the present disclosure, errors and deviations in driving time can be reduced by determining inlet occlusion using a filtering time obtained by filtering a predetermined number of consecutive driving times, so that whether an inlet is occluded can be more accurately determined.

In addition, erroneous determination due to noise can be prevented by determining that inlet occlusion of a medical liquid injection device occurs only when both a condition that a filtering time tends to increase and a condition that the filtering time is greater than or equal to a predetermined value are satisfied.

According to one of the other problem solving means of the present disclosure, an erroneous determination that inlet occlusion of a medical liquid injection device occurs even when the inlet occlusion does not actually occur, due to a driving-time error due to temperature can be prevented by compensating for a driving time on the basis of a temperature of the medical liquid injection device.

According to one of the other problem solving means of the present disclosure, whether an inlet is occluded can be more accurately determined by adjusting detection sensitivity on the basis of an injection rate of a medical liquid injection device.

According to one of the other problem solving means of the present disclosure, when an internal pressure of a medical liquid injection device is instantaneously increased due to other reasons in addition to inlet occlusion, driving of a pump module can be delayed so that an erroneous determination that the inlet occlusion occurs can be prevented.

DETAILED DESCRIPTION

Figure 1:
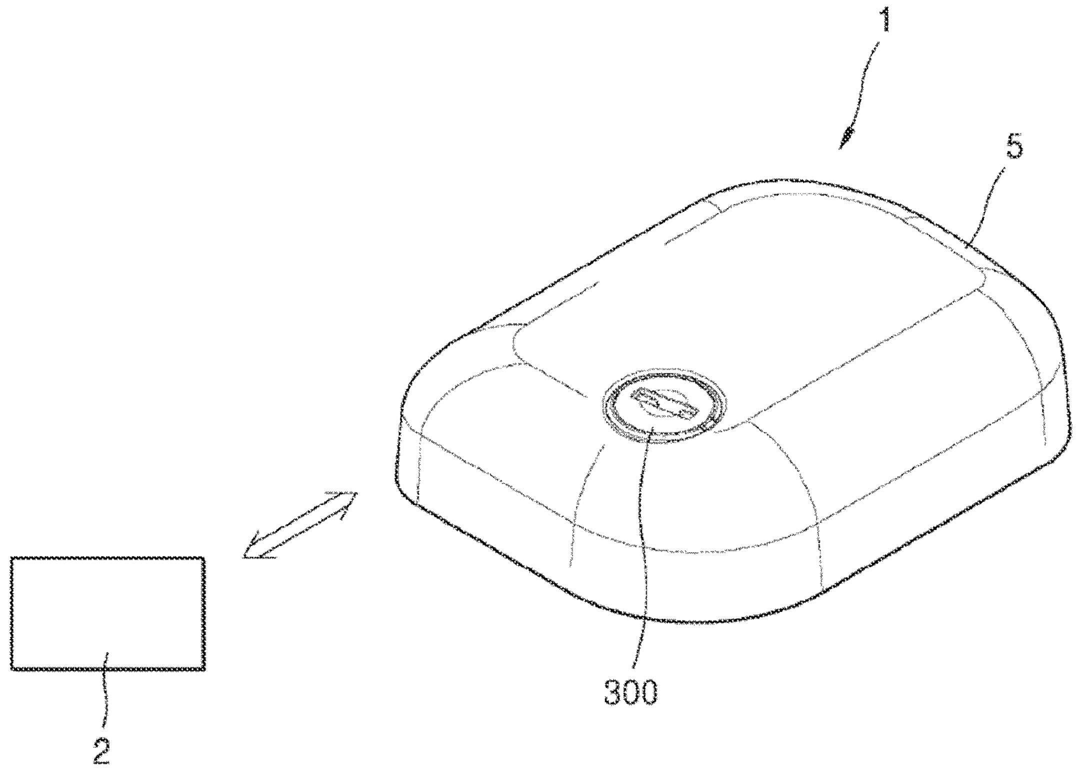
FIG. 1 is a perspective view illustrating a medical liquid injection device according to an embodiment.

A medical liquid injection device may include a pump module, a pivot fitting, at least one sensor, and a processor. The pump module may include a shaft that performs a linear reciprocating movement along one direction. The pivot fitting may include a first end connected to the shaft and a second end that rotationally reciprocates by the linear reciprocating movement. The at least one sensor may obtain contact time information on a time at which the at least one sensor comes into contact with the second end. The processor may calculate driving time of the pump module using the contact time information, and determine the occurrence of occlusion of the medical liquid injection device on the basis of the driving time.

Mode of Disclosure

Hereinafter, embodiments of the present disclosure will be described in detail with reference to the accompanying drawings such that those skilled in the art can easily carry out the present disclosure. The present disclosure may, however, be implemented in many different forms and should not be construed as limited to the embodiments set forth herein. In addition, in order to clearly describe the present disclosure in the drawings, parts which are not related to the description are omitted, and similar parts are denoted by similar reference numerals throughout the specification.

Throughout the specification, when a part is referred to as being "connected" to another part, it includes not only being directly connected, but also being "electrically connected" by interposing the other part therebetween. It should also be understood that when a part "includes" an element, unless there is another opposite description thereto, the part does not exclude another element but may further include the other element.

Hereinafter, the present disclosure will be described in detail with reference to the accompanying drawings.

FIG. 1 is a perspective view illustrating a medical liquid injection device 1 according to an embodiment.

Referring to FIG. 1, the medical liquid injection device 1 is attached to a medical liquid injection subject, and may inject a medical liquid stored therein to a user in a set amount. In an optional embodiment, the medical liquid injection device 1 may be mounted on a user's body. In addition, as another optional embodiment, the medical liquid injection device 1 may be mounted on an animal to inject a medical liquid.

The medical liquid injection device 1 may be used for various purposes depending on the type of a medical liquid to be injected. For example, the medical liquid may include an insulin-based medical liquid for a diabetic patient, and may include a medical liquid for other pancreas, a medical liquid for heart, and other various types of medical liquids.

The medical liquid injection device 1 may be connected to a remote device 2 connected by wire or wirelessly. A user may use the medical liquid injection device 1 by manipulating the remote device 2, and may monitor the state of use of the medical liquid injection device 1. For example, the amount of medical liquid injected from the medical liquid injection device 1, the number of injections of the medical liquid, the amount of medical liquid stored in a reservoir 200, user's bio information, and the like may be monitored, based on this, the user may drive the medical liquid injection device 1.

In an embodiment, the remote device 2 refers to a communication terminal capable of using an application in a wired or wireless communication environment. Here, the remote device 2 may be a user's portable terminal. In more detail, the remote device 2 may include a computer (e.g., desktop, laptop, tablet, or the like), a media computing platform (e.g., cable, satellite set-top box, digital video recorder), a handheld computing device (e.g., personal digital assistant (PDA), e-mail client, or the like), a mobile phone in any form, a form of a wearable device that can be attached or mounted on the user's body, or any form of another kind of computing or communication platform, but the present disclosure is not limited thereto.

The medical liquid injection device 1 and the remote device 2 may communicate through a communication network. In this case, the communication network refers to a communication network providing an access path so that the remote device 2 may transmit and receive data after accessing a service server (not shown). The communication network may include, for example, a wired network such as a local area network (LAN), a wide area network (WAN), a metropolitan area network (MAN), and an integrated service digital network (ISDN), and a wireless network such as a wireless LAN, a code division multiple access (CDMA) network, a Bluetooth network, and a satellite communication network, but the scope of the present disclosure is not limited thereto.

According to FIG. 1, the remote device 2 is illustrated as being a single device, but the present disclosure is not necessarily limited thereto, and may include a plurality of devices capable of communicating with the medical liquid injection device 1.

Figure 2A:
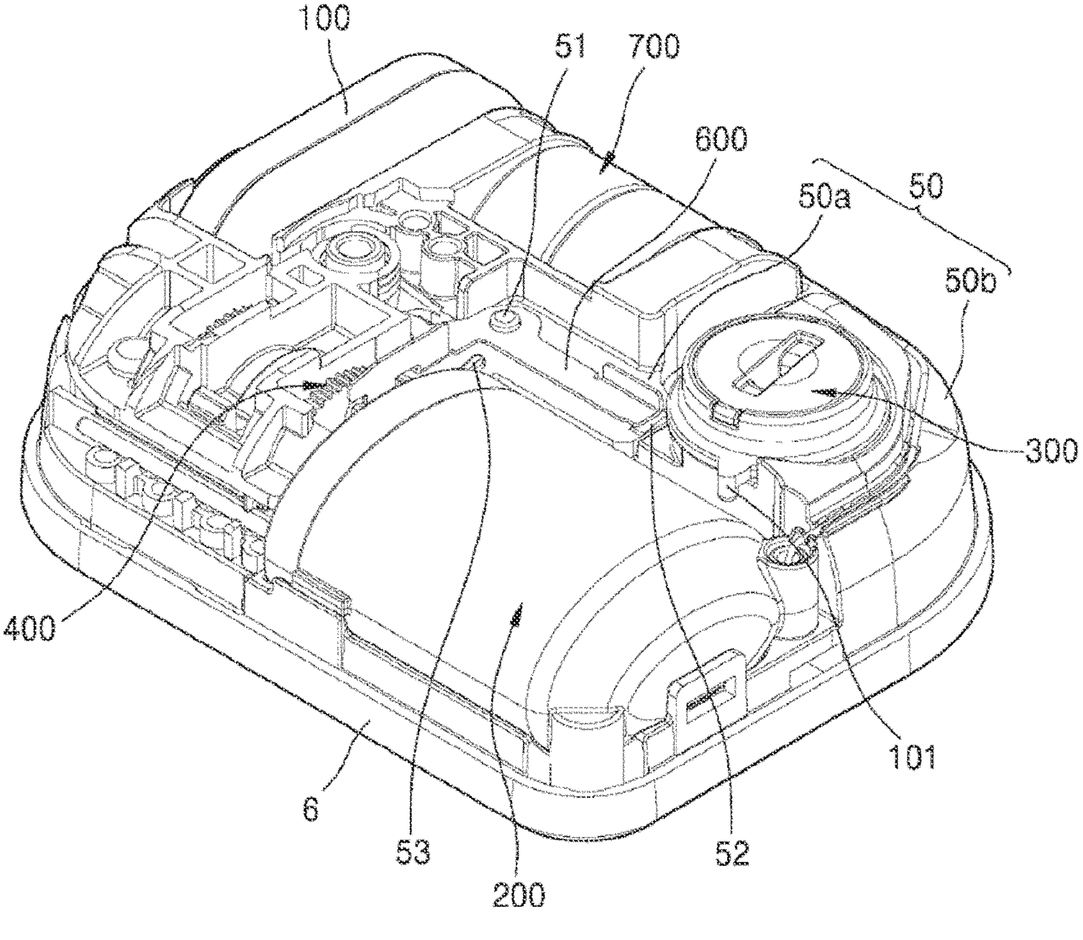
FIG. 2A is a perspective view illustrating an internal arrangement of the medical liquid injection device of FIG. 1.
Figure 2B:
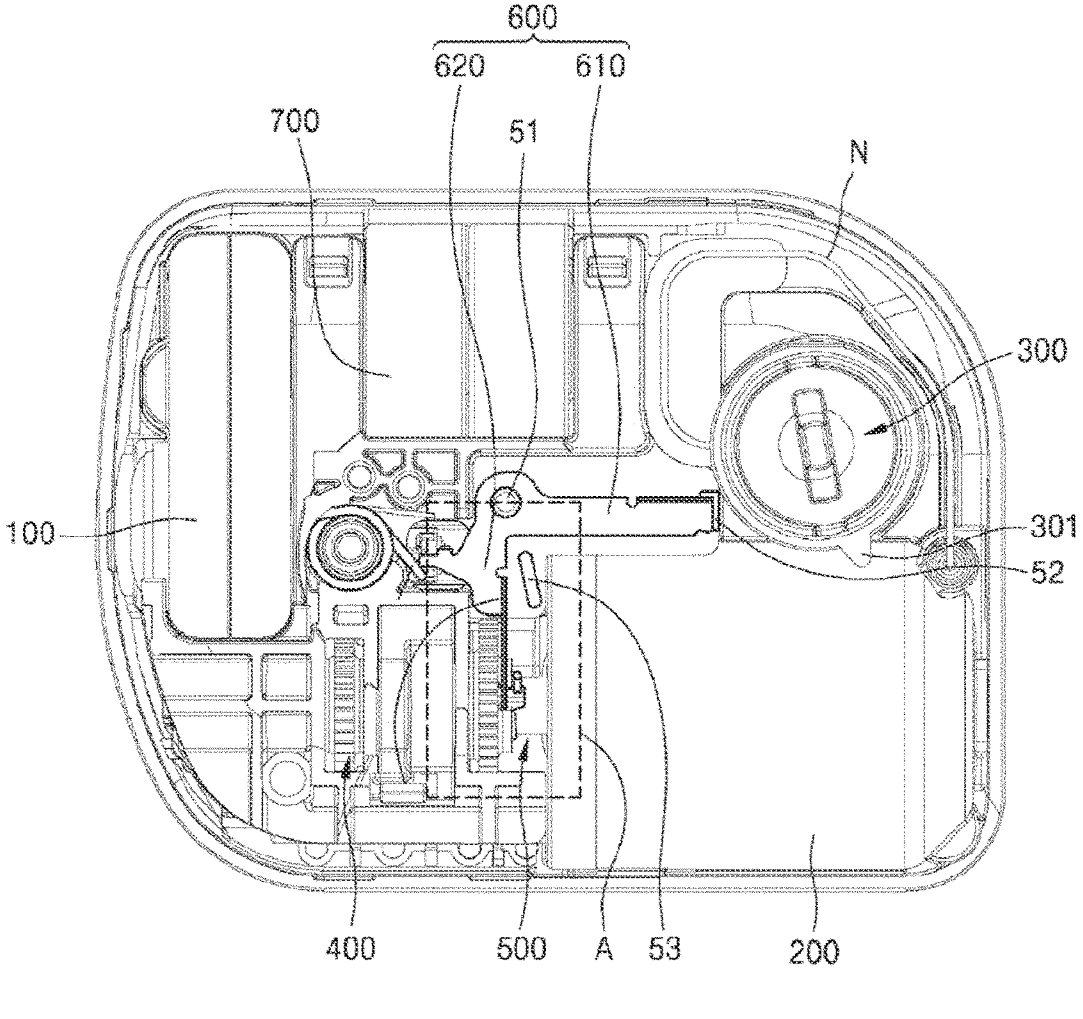
FIG. 2B is a plan view illustrating the medical liquid injection device of FIG. 2A.

FIG. 2A is a perspective view illustrating an internal arrangement of the medical liquid injection device of FIG. 1, and FIG. 2B is a plan view illustrating the medical liquid injection device of FIG. 2A.

Referring to FIGS. 2A and 2B, one embodiment of the medical liquid injection device 1 may include a housing 5 covering an outside, and an attachment part 6 located adjacent to the user's skin. The medical liquid injection device 1 includes a plurality of parts disposed in an inner space between the outer housing 5 and the attachment part 6. A separate bonding means may be further interposed between the attachment part 6 and the user's skin, and the medical liquid injection device 1 may be fixed to the skin by the bonding means.

The medical liquid injection device 1 may include a base body 50, a pump module 100, the reservoir 200, a needle assembly 300, a driving unit 400, a clutch unit 500, a trigger member 600, and a battery 700.

The base body 50 forms a basic frame of the outer housing 5 and is mounted in the inner space of the outer housing 5. The base body 50 may be provided in plural. In an embodiment, a first body 50*a* covering an upper side of the internal parts and a second body 50*b* covering a lower side of the internal parts may be provided. The first body 50*a* and the second body 50*b* may be assembled and may fix the internal parts of the medical liquid injection device 1 to preset positions. In another embodiment, the base body may be formed of one integrated frame.

The base body 50 may provide a space in which the trigger member 600 can rotate. The base body 50 may support the trigger member 600, and the trigger member 600 may pivot about a pivot shaft 51 that protrudes from the base body 50.

The base body 50 may include a stopper configured to limit a pivot distance of the trigger member 600. A plurality of stoppers may be provided, and a movement distance of the trigger member 600 may be limited so that the trigger member 600 pivots up to a predetermined point. According to an embodiment, the stopper may include a first stopper 52 and a second stopper 53.

The first stopper 52 protrudes upward from the base body 50 and is disposed adjacent to the needle assembly 300. The first stopper 52 is disposed to be in contact with a first end 610 of the trigger member 600, and may limit a rotation direction and a rotation distance of the first end 610 so that the first end 610 does not rotate in an opposite direction after rotating in one direction.

In detail, the first stopper 52 may be formed such that a surface thereof coming into contact with the trigger member 600 protrudes to be inclined. When the first end 610 of the trigger member 600 pivots in one direction, the first end 610 moves along an upper surface of the first stopper 52. The upper surface of the first stopper 52 guides the movement of the trigger member 600, and thus the needle assembly 300 may smoothly pivot as the trigger member 600 rotates.

The first stopper 52 may limit a pivoting direction of the trigger member 600. A sidewall of the first stopper 52 may extend from the upper surface and formed substantially perpendicular to a plane of the base body 50. The sidewall may secure the stability of the medical liquid injection device 1 by preventing the needle assembly 300 and the trigger member 600 from rotating in the opposite direction after the trigger member 600 rotates by a predetermined rotation distance in one direction.

The second stopper 53 is disposed adjacent to the reservoir 200, the driving unit 400, and the clutch unit 500. The second stopper 53 may be disposed to protrude upward from the base body 50 and may limit a movement distance of a second end 620 of the trigger member 600. In an embodiment, the second stopper 53 includes a longitudinal extension line that may pass through a center of the pivot shaft 51.

Meanwhile, in a process of injecting a medical liquid in the reservoir 200 to a user through a needle N of the needle assembly 300, there may occur a case in which an inlet, which is a passage through which the medical liquid is injected, is occluded due to various foreign substances or blood coagulation around the needle. The inlet may include an internal passage of the needle N or a medical liquid movement passage connecting the needle N to the reservoir 200, but the present disclosure is not limited thereto. When the inlet is occluded due to such causes, a medical liquid in an amount required for a user may not be injected. Alternatively, a medical liquid may not be injected into the user at all.

In an embodiment, the medical liquid injection device 1 may determine whether the inlet is occluded on the basis of a driving time of the pump module 100.

For example, when the driving time of the pump module 100 exceeds a threshold value, the inlet may be determined to be occluded.

Figure 3:
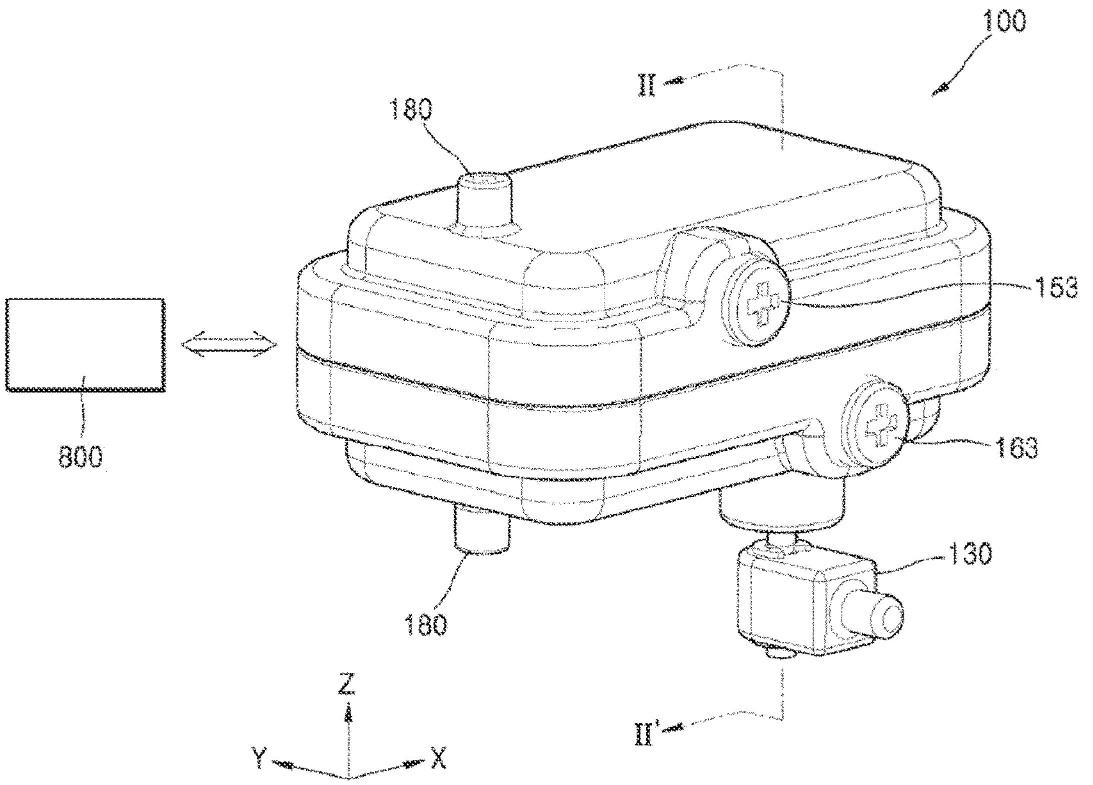
FIG. 3 is a perspective view of a pump module according to an embodiment of the present disclosure.
Figure 4:
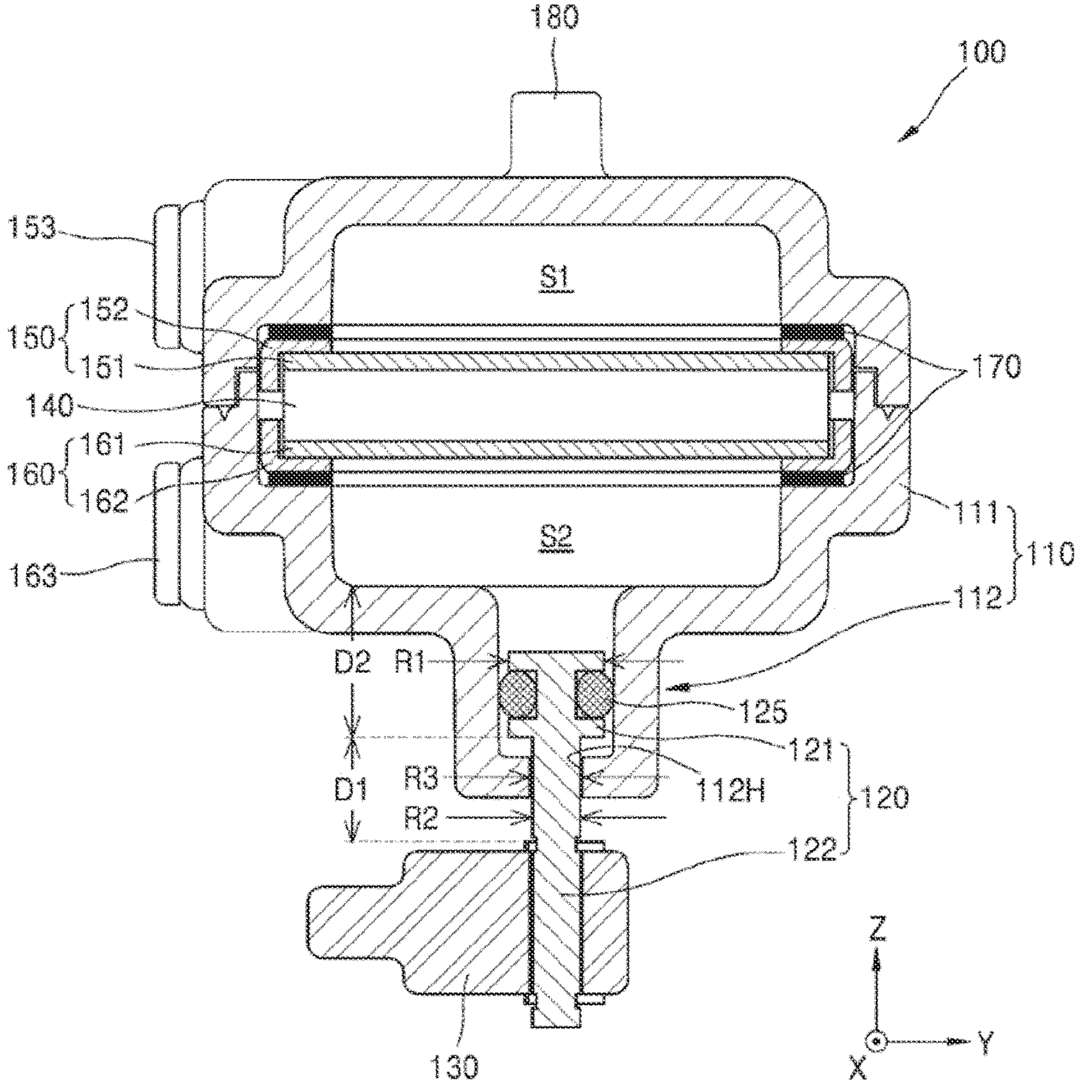
FIG. 4 is a cross-sectional view taken along line II-II' of FIG. 3.

FIG. 3 is a perspective view of the pump module according to an embodiment of the present disclosure. FIG. 4 is a cross-sectional view taken along line II-II' of FIG. 3.

Referring to FIG. 3, a processor 800 may allow the pump module 100 of the present disclosure to perform overall operations. Specifically, the processor 800 may calculate the driving time or the like of the pump module 100 on the basis of information sensed by the pump module 100, and may determine the occurrence of occlusion of the medical liquid injection device 1 on the basis of the calculation result.

Although the processor 800 is illustrated in FIG. 3 as being implemented as a separate component from the pump module 100, according to another embodiment of the present disclosure, the processor 800 may be implemented as a component included in the pump module 100. When the processor 800 is implemented as a separate component from the pump module 100, the processor 800 may be included in the medical liquid injection device 1, and the processor 800 may also be included in the remote device 2 and communicate with the medical liquid injection device 1 through a communication network.

The communication network may include, for example, a wired network such as a LAN, a WAN, a MAN, and an ISDN, and a wireless network such as a wireless LAN, a CDMA network, a Bluetooth network, and a satellite communication network, but the scope of the present disclosure is not limited thereto.

In addition, the processor 800 may be implemented as a digital signal processor (DSP) for processing a digital signal, a microprocessor, or a time controller (TCON). However, the processor is not limited thereto, and may include one or more of a central processing unit (CPU), a micro controller unit (MCU), a micro processing unit (MPU), a controller, an application processor (AP), or a communication processor (CP), an ARM processor, or may be defined by corresponding terms. In addition, the processor 800 may be implemented as a system on chip (SoC) having a built-in processing algorithm, large scale integration (LSI), or a field programmable gate array (FPGA).

Referring to FIGS. 3 and 4, an inner housing 110 of the pump module 100 may include a shaft hole 112H provided at one side thereof, and a shaft 120 having a predetermined length may extend to an outside of the inner housing 110 through the shaft hole 112H. In an embodiment, the shaft hole 112H may be formed in a protrusion 112 that extends to one side with respect to a main body 111 of the inner housing 110, and a diameter of the protrusion 112 may be less than that of the main body 111.

A first portion 121 of the shaft 120 is disposed inside the inner housing 110, and a second portion 122 extends to the outside of the inner housing 110 after passing through the shaft hole 112H as described above. The shaft 120 may reciprocate in an up-and-down direction (Z direction) in FIGS. 3 and 4. When the shaft 120 reciprocates, the first portion 121 may linearly reciprocate in an inner space of the inner housing 110, for example, an inner space corresponding to the protrusion 112. A diameter R1 of the first portion 121 of the shaft 120 is greater than a diameter R3 of the shaft hole 112H, and thus the first portion 121 does not fall out of the inner housing 110.

The second portion 122 of the shaft 120 has a diameter R2 that is less than the diameter R3 of the shaft hole 112H, and in order to prevent the second portion 122 from falling out of the shaft hole 112H, the second portion 122 may be coupled to a power transmission unit 130 that is provided outside the inner housing 110.

A first sealing material 125 may be disposed on a side surface of the first portion 121 of the shaft 120. The inner space of the inner housing 110, e.g., a space defined by an inner surface of the inner housing 110 and an inner surface of the shaft 120, is a sealed space, and there is a fluid in the inner space, and the first sealing material 125 may prevent leakage (escape) of the fluid through a gap between the inner housing 110 and the shaft 120. In FIG. 4, the fluid is omitted for convenience of description.

According to an embodiment, as shown in FIG. 4, the first sealing material 125 may be an O-ring type that may cover the side surface of the first portion 121, and the leakage of the fluid in the inner housing 110 to the outside of the inner housing 110 through the shaft hole 112H may be prevented by the first sealing material 125. The leakage of the fluid may be effectively prevented by forming a first distance D1 from the first portion 121 of the shaft 120 to the power transmission unit 130 to be equal to or less than an internal length D2 of the protrusion 112.

A membrane 140 may be disposed in the inner space of the inner housing 110, e.g., the inner space corresponding to the main body 111. The inner space includes a first space S1 and a second space S2 respectively located on opposite sides of the membrane 140. In FIG. 4, a space farther from the shaft 120 based on the membrane 140 is represented as the first space S1 and a space closer to the shaft 120 based on the membrane 140 is represented as the second space S2.

The membrane 140 may have a porous structure through which the fluid and ions may pass. The membrane 140 may be, for example, a frit-type membrane that is fabricated by sintering spherical silica with heat. For example, the spherical silica used to form the membrane may have a diameter of about 20 nm to about 500 nm, in particular, a diameter of about 30 nm to about 300 nm, and in more particular, a diameter of about 40 nm to about 200 nm. When the diameter of the spherical silica satisfies the above range, a pressure caused by a first fluid passing through the membrane 140, that is, a sufficient pressure to move the shaft 120, may be generated.

In the above embodiment, the membrane 140 includes the spherical silica, but the membrane 140 is not limited thereto. In another embodiment, a kind of a material included in the membrane 140 is not particularly limited as long as the material is a material that may cause an electrokinetic phenomenon due to zeta potential, for example, porous silica or porous alumina.

The membrane 140 may have a thickness of about 20 μm to about 10 mm, in particular, about 300 μm to about 5 mm, and in more particular, about 1000 μm to about 4 mm.

A first electrode body 150 and a second electrode body 160 are respectively arranged on opposite sides of the membrane 140. The first electrode body 150 may include a first porous plate 151 and a first electrode strip 152 disposed on a first side of the membrane 140. The second electrode body 160 may include a second porous plate 161 and a second electrode strip 162 disposed on a second side of the membrane 140.

The first and second porous plates 151 and 161 may be disposed to be respectively in contact with opposite main surfaces of the membrane 140. The first and second porous plates 151 and 161 may effectively move the fluid and the ions through the porous structure. The first and second porous plates 151 and 161 may each have a structure in which an electrochemical reaction material is formed on a porous base layer. The electrochemical reaction material may be formed by being electrodeposited or coated on the porous base layer by a method such as electroless plating, vacuum deposition, coating, sol-gel process, or the like.

The porous base layer may be an insulator. For example, the porous base layer may include one or more selected from non-conductive ceramic, a non-conductive polymer resin, non-conductive glass material, and a combination thereof.

The non-conductive ceramic may include, for example, one or more selected from the group consisting of rock wool, gypsum, ceramics, cement, and a combination thereof, and in particular, one or more selected from the group consisting of rock wool, gypsum, and a combination thereof, but the present disclosure is not limited thereto.

The non-conductive polymer resin may include one or more selected from the group consisting of: for example, synthetic fiber selected from the group consisting of polypropylene, polyethylene terephthalate, polyacrylonitrile, and a combination thereof; natural fiber selected from the group consisting of wool, cotton, and a combination thereof; a sponge; an organism, e.g., a porous material derived from a bone of an organism; and a combination thereof, but the present disclosure is not limited thereto.

The non-conductive glass may include one or more selected from the group consisting of glass wool, glass frit, porous glass, and a combination thereof, but the present disclosure is not limited thereto.

The porous base layer may have a pore size of about 0.1 μm to about 500 μm, in particular, about 5 μm to about 300 μm, and in more particular about 10 μm to about 200 μm. When the pore size of the porous support satisfies the above range, the fluid and the ions may be effectively moved, thereby improving stability, lifespan characteristics, and efficiency of the pump module 100.

The electrochemical reaction material may include a material that may generate a pair of reactions in which an oxidizing electrode and a reducing electrode exchange positive ions, e.g., hydrogen ions, during electrode reactions of the first and second electrode bodies 150 and 160, and at the same time, may constitute a reversible electrochemical reaction. The electrochemical reaction material may include one or more selected from the group consisting of, for example, silver/silver oxide, silver/silver chloride, MnO (OH), polyaniline, polypyrrole, polythiophene, polythionine, quinone-based polymer, and a combination thereof.

The first and second electrode strips 152 and 162 may be disposed at edges of the first and second porous plates 151 and 161, respectively, and may be respectively connected to first and second terminals 153 and 163 on the outside of the inner housing 110. The first and second electrode strips 152 and 162 may each include a conductive material such as silver, copper, or the like.

The fluid provided in the inner space of the inner housing 110 may include a first fluid and a second fluid having different phases from each other. The first fluid may include a liquid, such as water, and the second fluid may include a gas, such as air. The first fluid that exists in the inner space does not entirely fill the inner space. That is, a volume of the inner space is greater than a volume of the first fluid that exists in the inner space. A second fluid exists in a portion in which water does not exist in the inner space.

Second sealing materials 170 are respectively disposed at opposite sides of a structure including the membrane 140, the first electrode body 150, and the second electrode body 160. Each of the second sealing materials 170 may have a loop shape having an area corresponding to the edge of the structure described above. The fluid, e.g., the first fluid, moves from the first space S1 to the second space S2 or in the reverse direction along a thickness direction of the membrane 140 so as to pass through the membrane 140, and at this time, the second sealing material 170 blocks a gap between the inner surface of the inner housing 110 and the above structure to prevent the liquid from moving to the gap.

The fluid may be introduced into the inner space through a replenishing port 180 as shown in FIG. 3. In an embodiment, the first fluid is entirely filled in the inner space through replenishing ports 180 at opposite sides, and then, the first fluid is partially discharged through one replenishing port 180 and the replenishing ports 180 are closed, and thus, the first fluid and the second fluid may exist in the inner space of the inner housing 110.

Hereinafter, the behavior of the fluid and the movement of the shaft according to the behavior will be described with reference to FIGS. 5A to 6B.

Figure 5A:
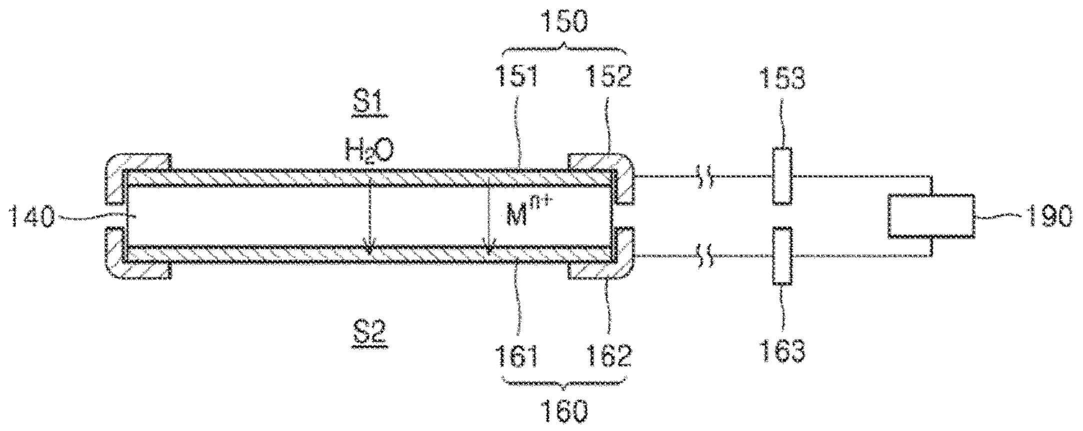
FIGS. 5A and 5B are schematic views illustrating reactions of first and second electrode bodies around a membrane.
Figure 5B:
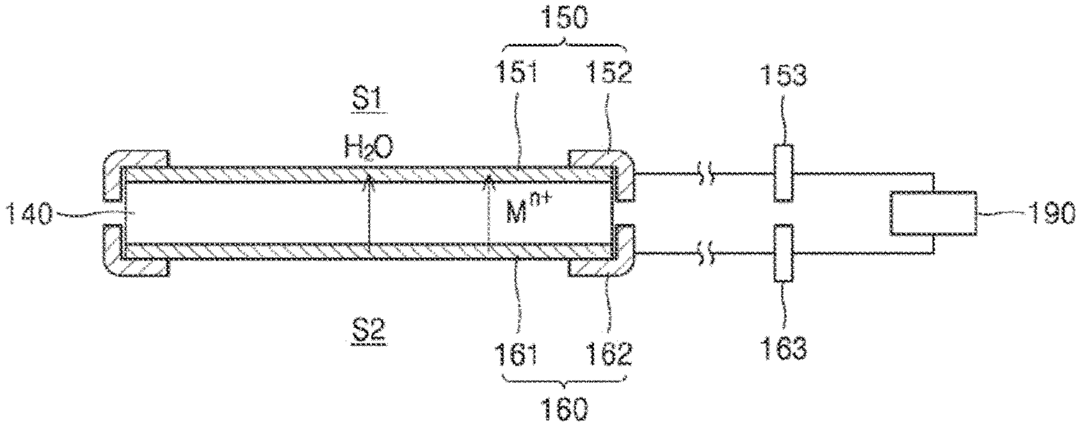

FIGS. 5A and 5B are schematic views illustrating reactions of the first and second electrode bodies around the membrane.

Referring to FIGS. 5A and 5B, the first electrode body 150 and the second electrode body 160 are electrically connected to a power supply unit 190 via first and second terminals 153 and 163, respectively. By supplying a voltage supplied by the power supply unit 190 after alternately changing the polarity of the voltage, a movement direction of the liquid such as water may be changed.

In an embodiment, a case in which the silver/silver oxide is used as the electrochemical reaction material and the first fluid is a solution including water will be described.

As shown in FIG. 5A, when the first electrode body 150 is an oxidizing electrode and the second electrode body 160 is a reducing electrode, a reaction of Ag(s)+H2O→Ag2O (s)+2H++2e− occurs in the first electrode body 150 and a reaction of Ag2O(s)+2H+2e−→Ag(s)+H2O occurs in the second electrode body 160.

Cations (Mn+, e.g., hydrogen ions) generated according to the oxidation reaction in the first electrode body 150 move toward the second electrode body 160 through the membrane 140 due to a voltage difference, and at this time, water (H2O) moves together with the cations and a predetermined pressure may be generated.

Thereafter, as shown in FIG. 5B, when the polarity of the voltage supplied by the power supply unit 190 is reversed, the electrochemical reaction material that has been consumed when the first electrode body 150 is previously used as the oxidizing electrode is recovered when the first electrode body 150 is used as the reducing electrode. Likewise, the electrochemical reaction material may be also recovered in the reducing electrode, and thus, the first and second electrode bodies 150 and 160 may continuously react accordingly to the voltage supply from the power supply unit 190. Unlike in FIG. 5A, when the polarity of the voltage supplied to the first and second electrode bodies 150 and 160 is reversed, as shown in FIG. 5B, the cations (Mn+, e.g., hydrogen ions) and the water (H2O) move from the second space S2 to the first space S1.

Figure 6A:
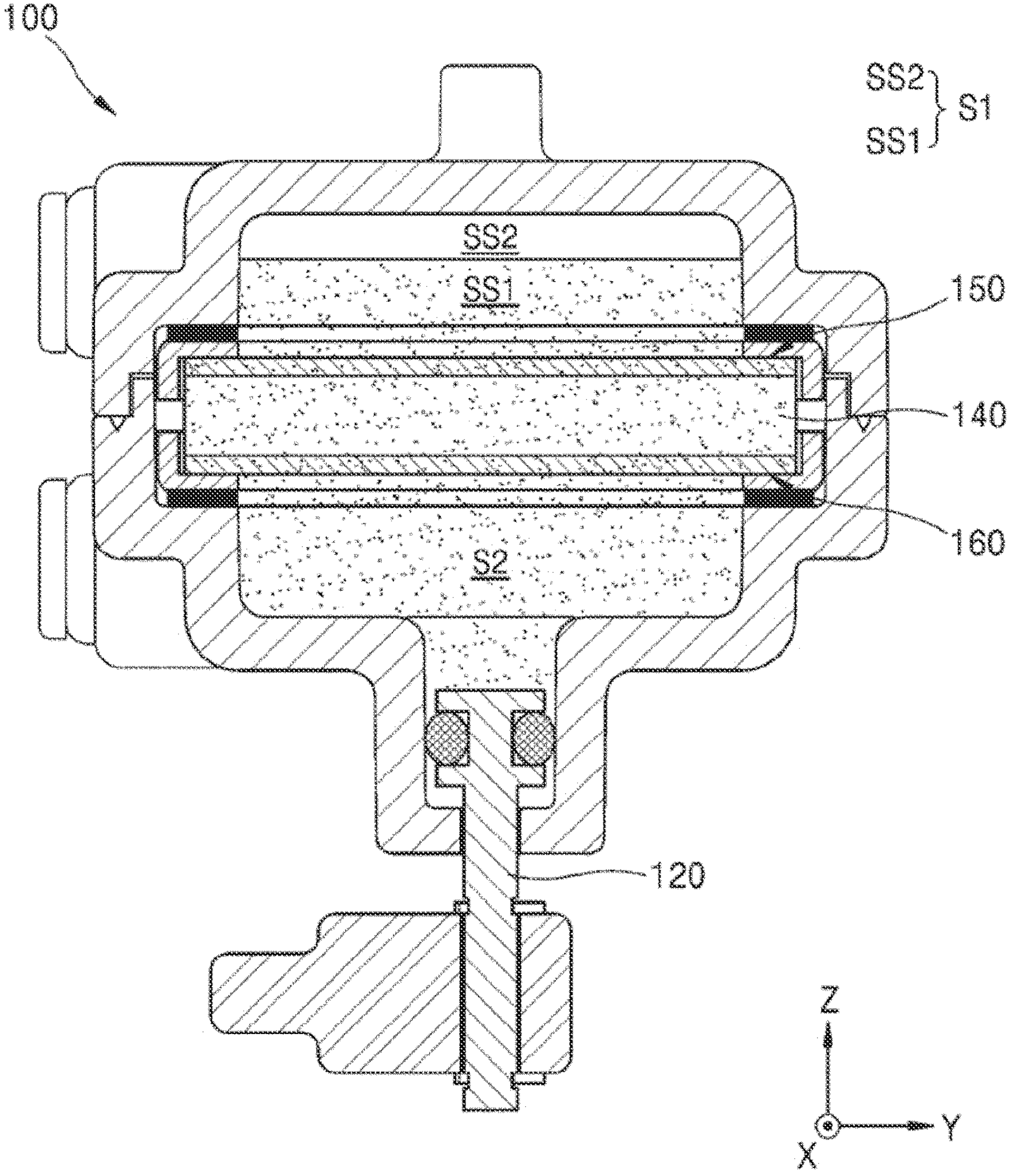
FIGS. 6A and 6B are cross-sectional views illustrating a reciprocating movement of a shaft.
Figure 6B:
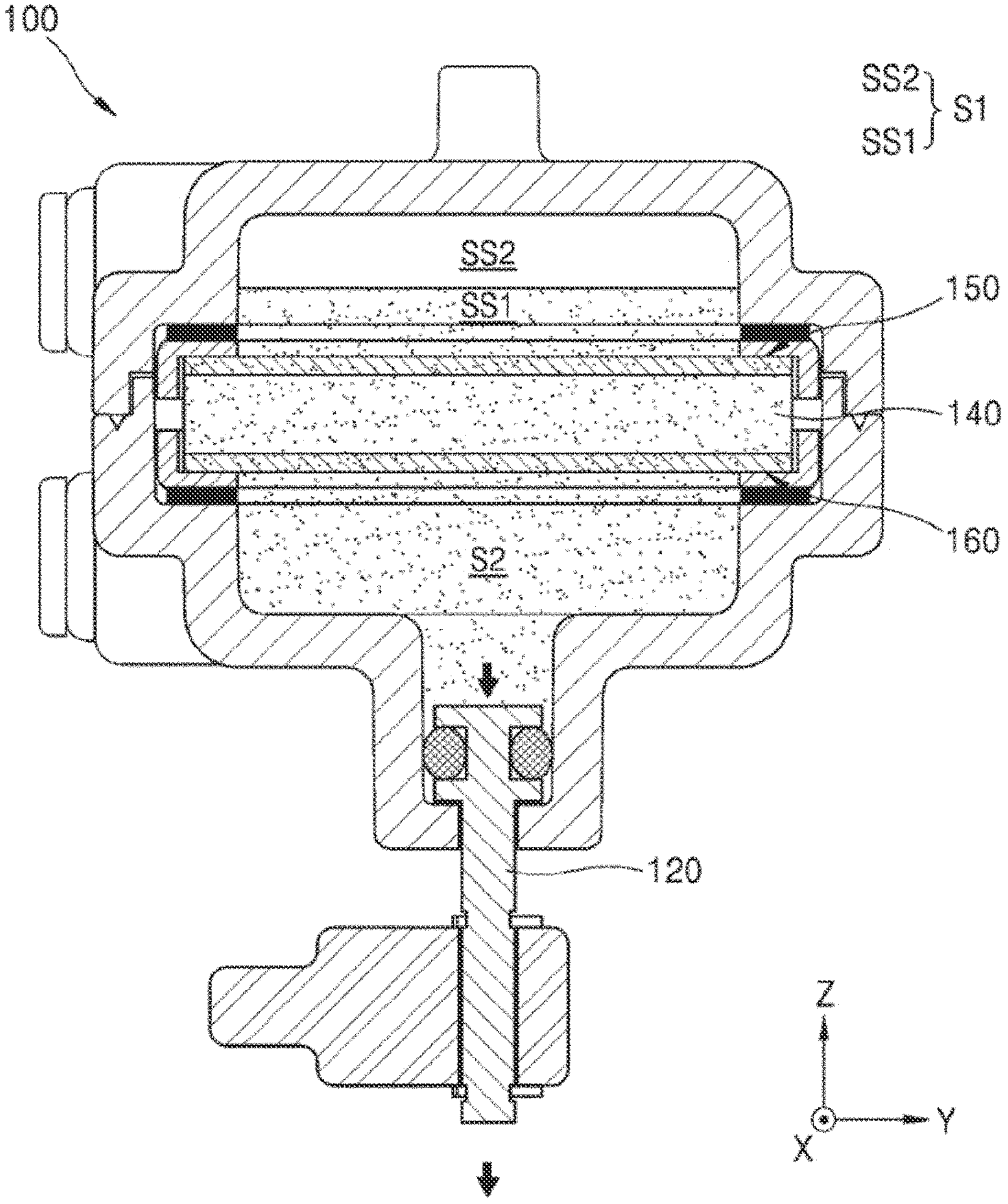

FIGS. 6A and 6B are cross-sectional views illustrating a reciprocating movement of the shaft.

FIG. 6A illustrates a state before the shaft moves and FIG. 6B illustrates a state after the shaft moves. FIG. 6A may be understood as a state before the voltage is applied to the first and second electrode bodies 150 and 160 by the power supply unit 190 as described above with reference to FIG. 5A.

Referring to FIG. 6A, the first fluid that is the liquid such as water exists in the inner space of the inner housing 110, and the volume of the first fluid in the inner space is less than the volume of the inner space. The second fluid including a gas such as the air exists in the region of the inner space, in which the liquid does not exist.

For example, the first fluid exists in each of the first and second spaces S1 and S2, and the first fluid and the second fluid coexist in the first space S1, while the volume of the first fluid in the first space S1 may be less than a volume of the first space S1. The first fluid also exists in the second space S2, but the second fluid does not exist, unlike the first space S1. Hereinafter, for convenience of description, in the first space S1, a space in which the first fluid, that is, the liquid, exists is referred to as a first sub-space SS1 and a space in which the second fluid, that is, the gas, exists is referred to as a second sub-space SS2. The first sub-space SS1 and the second sub-space SS2 may form the first space S1. For example, in the first space S1, a remaining space except for the first sub-space SS1 may be the second sub-space SS2.

In the state of FIG. 6A, when the power supply unit 190 supplies the voltage to the first and second electrode bodies 150 and 160, the reaction described above with reference to FIG. 5A occurs and the cations (e.g., hydrogen ions) move in a first direction (−Z direction in FIG. 4) from the first space S1 to the second space S2. At this time, a pressure is generated while the first fluid (e.g., H2O) in the first space S1 is moved with the cations in the first direction through the membrane 140, and the shaft 120 linearly moves in the first direction due to the pressure as shown in FIG. 6B. While the first fluid (e.g., H2O) in the first space S1 moves to the second space S2, a ratio of a volume of the first sub-space SS1 with respect to a volume of the first space S1 is reduced, whereas a ratio occupied by the second sub-space SS2 in the first space S1 increases.

On the contrary, when the power supply unit 190 changes the polarity of the voltage and supplies the voltage to the first and second electrode bodies 150 and 160 in the state of FIG. 6B, the cations (e.g., hydrogen ions) and the first fluid (e.g., water) move in a second direction (Z direction in FIG. 4) from the second space S2 to the first space S1, and the shaft 120 is moved back to the original position as shown in FIG. 6A.

When the power supply unit 190 alternately changes the polarity of the voltage supplied to the first and second electrode bodies 150 and 160, the shaft 120 moves in the first direction and then moves in the second direction, that is, a reverse direction of the first direction, and then, moves back in the first direction, that is, may reciprocate.

The reciprocating movement of the shaft 120 may be described as a change according to a ratio of the volume of the space in which the second fluid exists, that is, the volume of the second sub-space SS2, with respect to the first space S1.

Figure 7:
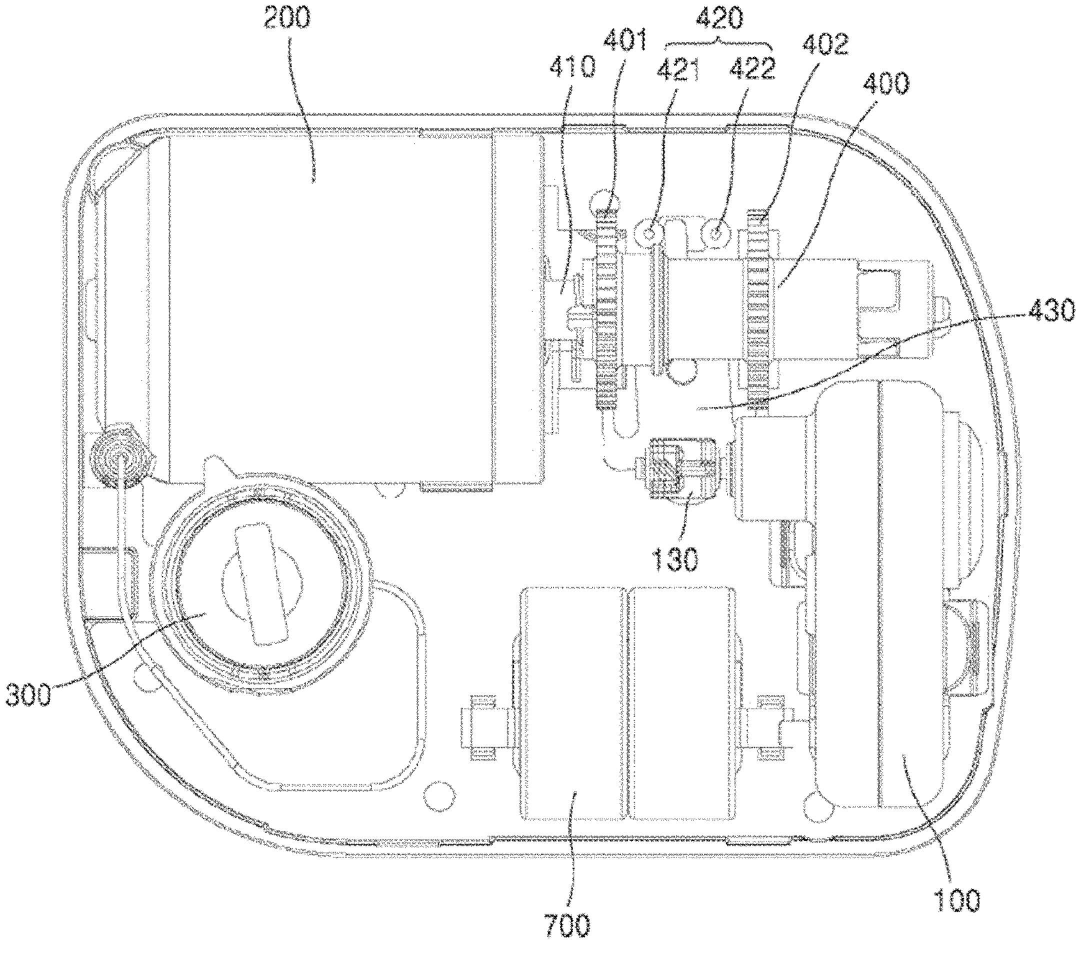
FIG. 7 is a plan view for describing injection of a medical liquid through a pump module and a driving unit by the medical liquid injection device according to an embodiment of the present disclosure.
Figure 8:
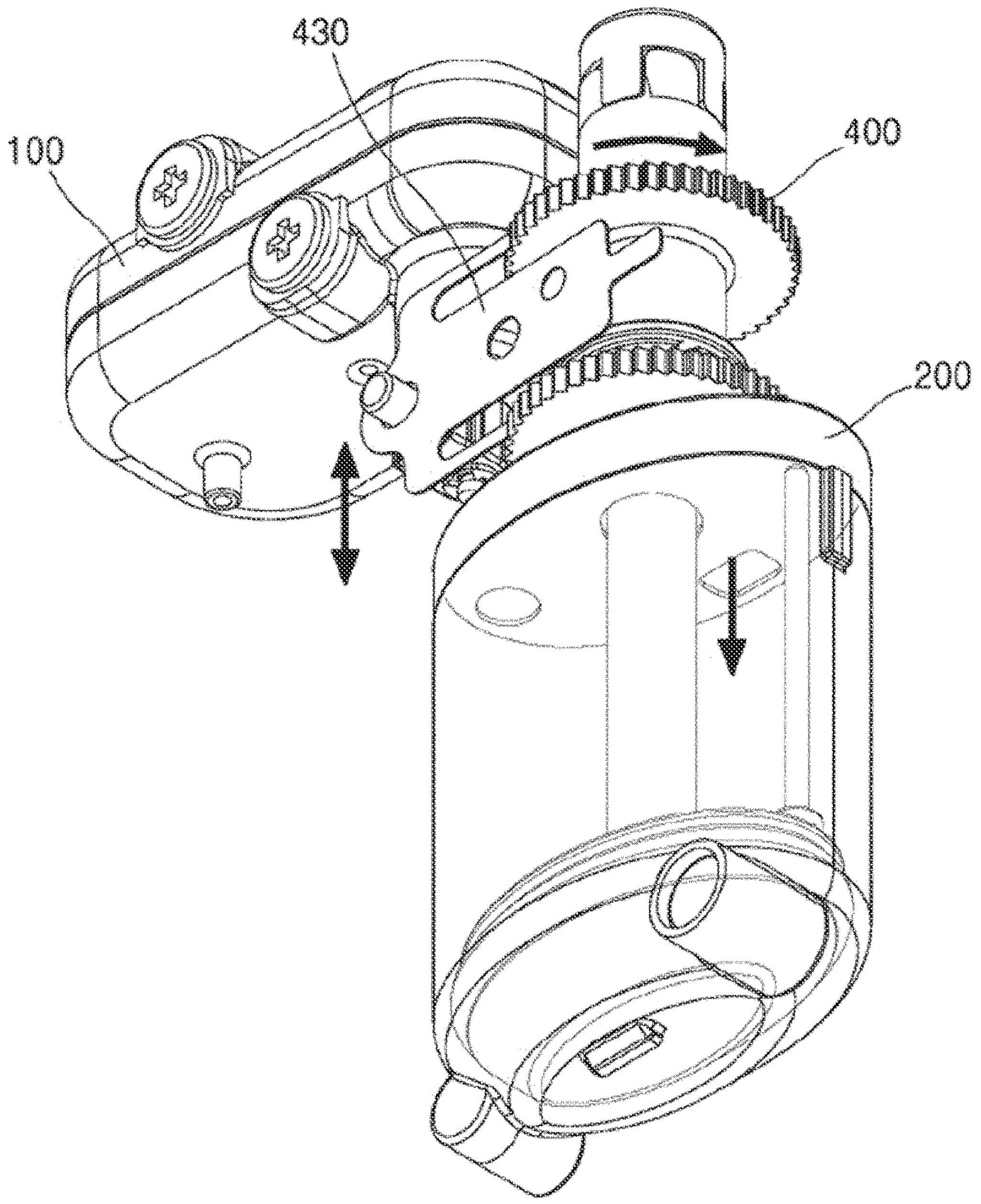
FIG. 8 is a perspective view for describing the injection of the medical liquid through the pump module and the driving unit by the medical liquid injection device according to an embodiment of the present disclosure.
Figure 9:
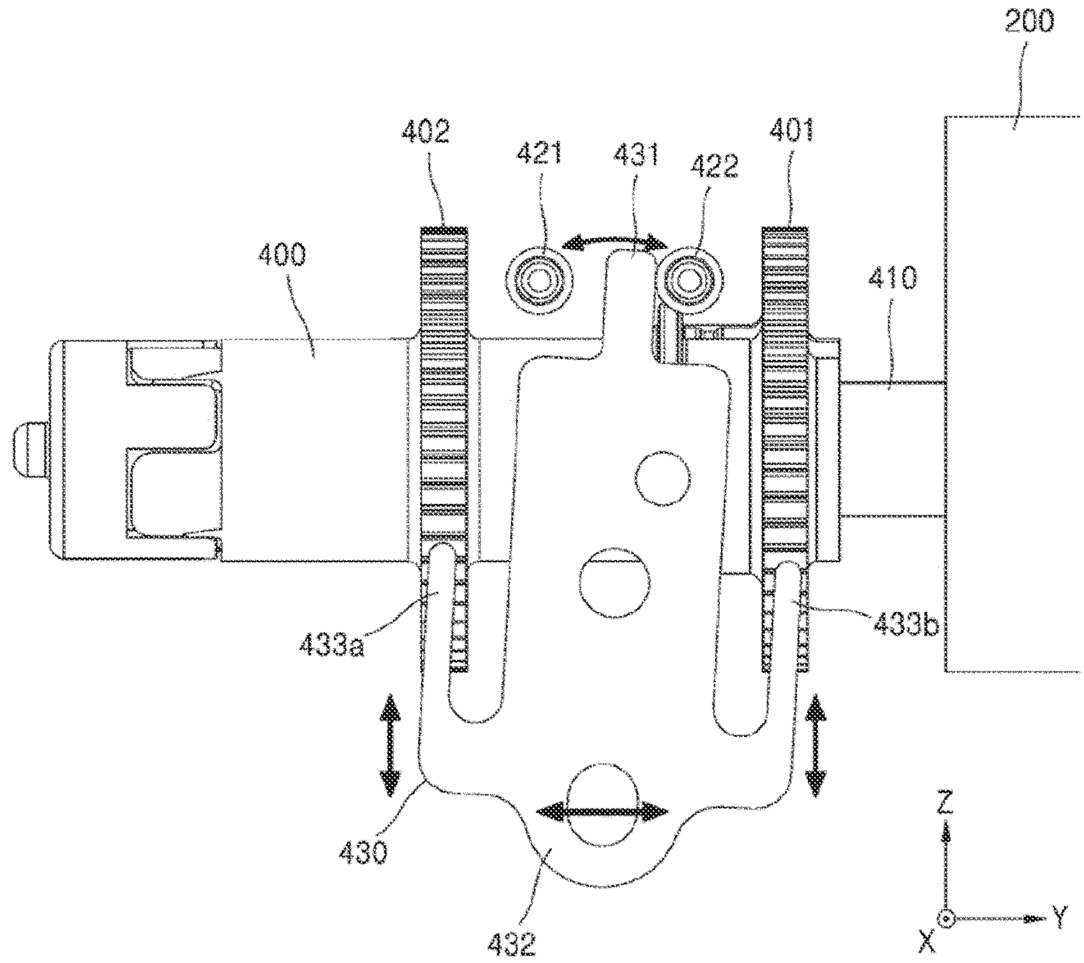
FIG. 9 is a plan view for describing an operation of the driving unit according to an embodiment of the present disclosure.

FIG. 7 is a plan view for describing injection of a medical liquid through the pump module and the driving unit by the medical liquid injection device according to an embodiment of the present disclosure. FIG. 8 is a perspective view for describing the injection of the medical liquid through the pump module and the driving unit by the medical liquid injection device according to an embodiment of the present disclosure. FIG. 9 is a plan view for describing an operation of the driving unit according to an embodiment of the present disclosure.

Referring to FIGS. 7 to 9, the power transmission unit 130 may be connected to a pivot fitting 430. Here, the pivot fitting 430 may include a first end 431, a second end 432, and third ends 433*a* and 433*b*. The first end 431 may be a portion in contact with at least one of sensors 421 and 422, the second end 432 may be a portion connected to the power transmission unit 130, and the third ends 433*a* and 433*b* may be portions in contact with a first connection end 401 and a second connection end 402, respectively.

The at least one of the sensors 421 and 422 according to an embodiment of the present disclosure may be an anchor sensor, but is not limited thereto, and may be implemented through any type of sensor capable of sensing through a contact operation.

The pump module 100 of the present disclosure may linearly reciprocate the shaft 120 as described with reference to FIGS. 3 to 6B, and accordingly, the power transmission unit 130 connected to the second portion 122 of the shaft may also perform a linear reciprocating movement in the same direction.

That is, the power transmission unit 130 may be connected to the second end 432 of the pivot fitting 430, and the second end 432 may also perform a linear reciprocating movement according to the linear reciprocating movement of the power transmission unit 130.

As in the example of FIG. 9, when the second end 432 performs a linear movement in a right direction (Y direction) by the reciprocating movement of the pump module 100 in a state in which the first end 431 is in contact with a second sensor 422, the pivot fitting 430 may perform a rotational movement. The third end 433*b* of the pivot fitting 430 adds force to a gear of the first connection end 401 while moving in an upward direction (Z direction), so that the driving unit 400 may rotate. In addition, the first end 431 of the pivot fitting 430 may perform a rotational movement to the left (in a-Y direction) until coming into contact with a first sensor 421, and the rotational movement of the pivot fitting 430 is stopped when the first end 431 comes into contact with the first sensor 421.

Similarly, when the second end 432 performs a linear movement in a left direction (−Y direction) by the reciprocating movement of the pump module 100 in the state in which the first end 431 is in contact with the first sensor 421, the pivot fitting 430 may perform a rotational movement. The third end 433*b* of the pivot fitting 430 adds force to a gear of the second connection end 402 while moving in the upward direction (Z direction), so that the driving unit 400 may rotate. In addition, the first end 431 of the pivot fitting 430 may perform a rotational movement to the right (in the Y direction) until coming into contact with the second sensor 422, and the rotational movement of the pivot fitting 430 is stopped when the first end 431 comes into contact with the second sensor 422.

As described above, a connecting shaft 410 formed to extend from the driving unit 400 toward the reservoir 200 is connected to the driving unit 400 and rotates in response to the rotation of the driving unit 400.

That is, as shown in FIG. 9, the linear reciprocating movement in the pump module 100 transmitted through the power transmission unit 130 may be converted into a rotational reciprocating movement of the driving unit 400, and the medical liquid injection device 1 according to an embodiment of the present disclosure may inject the medical liquid stored in the reservoir 200 through the rotational reciprocating movement.

The processor 800 according to an embodiment of the present disclosure may obtain contact time information detected through the sensors 421 and 422.

Referring to the example of FIG. 9, the processor 800 may obtain first contact time information on a time at which the first end 431 is separated from contact with the second sensor 422, and obtain second contact time information on a time at which the first end 431 comes into contact with the first sensor 421. Thereafter, the processor 800 may calculate a first driving time of the pump module 100 on the basis of the first and second contact time information described above. Here, the first driving time may be a driving time for driving a push operation of the pump module 100.

Similarly, the processor 800 may obtain third contact time information on a time at which the first end 431 is separated from contact with the first sensor 421, and obtain fourth contact time information on a time at which the first end 431 comes into contact with the second sensor 422. Thereafter, the processor 800 may calculate a second driving time of the pump module 100 on the basis of the third and fourth contact time information described above. Here, the second driving time may be a driving time for driving a pull operation of the pump module 100.

Meanwhile, the above-described first and second driving times (a push driving time and a pull driving time) may be affected by various elements such as membrane, mechanism, frictional force, length, temperature, load, electrolysis, and the like.

Figure 10:
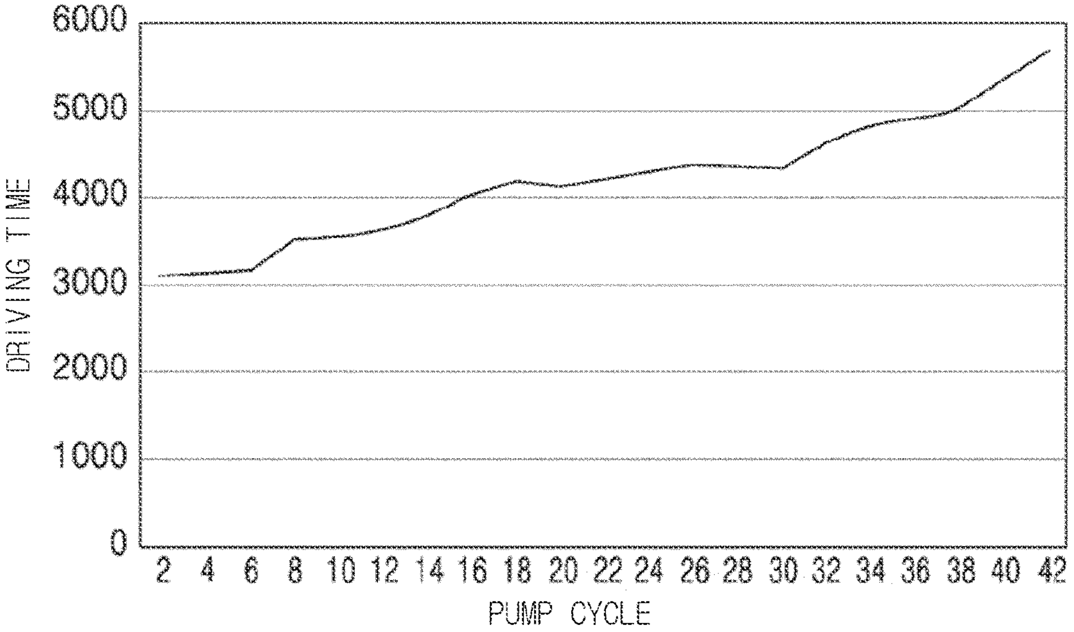
FIG. 10 is a view for describing a correlation between an internal pressure of the medical liquid injection device and a driving time of the pump module according to an embodiment.

FIG. 10 is a view for describing a correlation between an internal pressure of the medical liquid injection device and a driving time of the pump module according to an embodiment.

The driving time of the pump module may be changed by various causes.

For example, the driving time of the pump module may be changed according to whether an inlet, which is a passage through which a medical liquid is injected, is occluded. Specifically, when inlet occlusion occurs, the internal pressure of the medical liquid injection device rises, and thus the driving time of the pump module may increase.

In addition, the driving time of the pump module may be changed according to a temperature of the medical liquid injection device. Specifically, in the same pressure condition, the driving time of the pump module may be increased when the temperature of the medical liquid injection device is lower than a reference temperature, and the driving time of the pump module may be reduced when the temperature of the medical liquid injection device is higher than the reference temperature.

In addition, the driving time of the pump module may be changed according to a medical liquid injection rate of the medical liquid injection device. Specifically, as the medical liquid injection rate increases, the internal pressure of the medical liquid injection device is increased, so that the driving time of the pump module may be increased.

In the graph shown in FIG. 10, an x-axis represents a pump cycle, and a y-axis represents the driving time of the pump module. One pump cycle may be referred to as completing one push operation and one pull operation of the pump module. A unit of driving time of the pump module may be ms (milliseconds). Referring to FIG. 10, when the internal pressure of the medical liquid injection device increases as the pump cycle continues, the driving time of the pump module tends to increase.

The method of calculating the driving time of the pump module has been described in detail with reference to FIG. 9, and thus a description thereof will be omitted.

Meanwhile, errors and deviations may occur whenever the driving time of the pump module is calculated, and hereinafter, a method of determining the occurrence of occlusion of the medical liquid injection device by minimizing the errors and deviations in driving time will be described.

Figure 11:
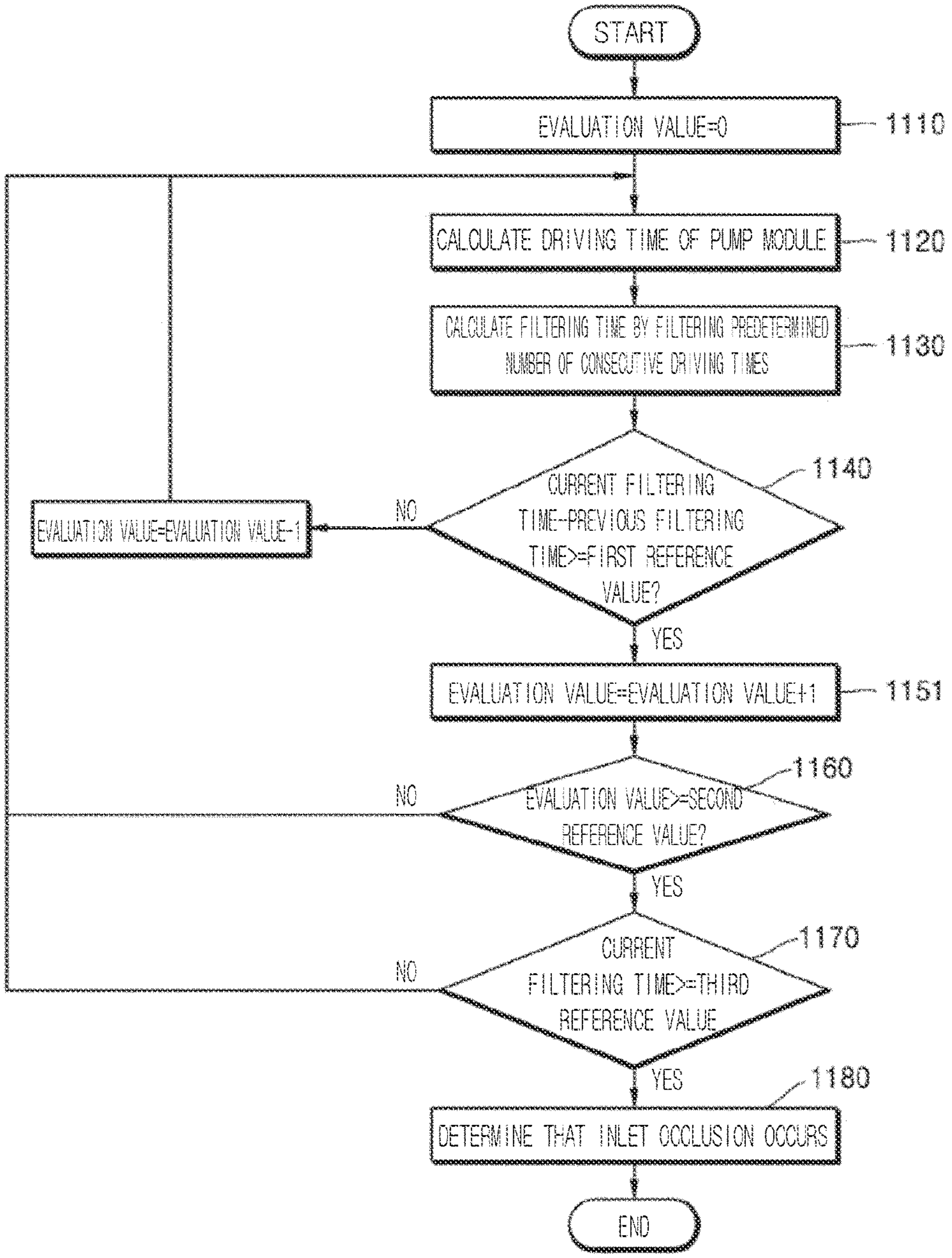
FIG. 11 is a flowchart of a method of determining the occurrence of inlet occlusion of the medical liquid injection device according to an embodiment.

FIG. 11 is a flowchart of a method of determining the occurrence of inlet occlusion of the medical liquid injection device according to an embodiment.

Referring to FIG. 11, in operation 1110, an evaluation value C may be set to zero. The evaluation value C is used to check an increase or decrease trend of the driving time of the pump module, which will be described below.

In operation 1120, the medical liquid injection device may calculate a driving time of the pump module.

Describing with reference to FIGS. 3 and 9, the processor 800 may obtain first contact time information on a time at which the first end 431 is separated from contact with the second sensor 422, and obtain second contact time information on a time at which the first end 431 comes into contact with the first sensor 421. Thereafter, the processor 800 may calculate a first driving time of the pump module 100 on the basis of the first and second contact time information described above. Here, the first driving time may be a driving time for driving a push operation of the pump module 100.

Similarly, the processor 800 may obtain third contact time information on a time at which the first end 431 is separated from contact with the first sensor 421, and obtain fourth contact time information on a time at which the first end 431 comes into contact with the second sensor 422. Thereafter, the processor 800 may calculate a second driving time of the pump module 100 on the basis of the third and fourth contact time information described above. Here, the second driving time may be a driving time for driving a pull operation of the pump module 100.

In operation 1130, the medical liquid injection device may calculate a filtering time by filtering a predetermined number of consecutive driving times.

The driving time used when calculating the filtering time may be the first driving time or the second driving time calculated in operation 1120. Alternatively, the driving time used when calculating the filtering time may use a longer driving time among the first driving time and the second driving time by comparing the first driving time and the second driving time calculated in operation 1120

For example, the medical liquid injection device may obtain 12 consecutive driving times and calculate a filtering time by applying a moving average method thereto. However, the number of the driving times and the filtering method used to calculate the filtering time are not limited to those in the above-described example.

In operation 1140, the medical liquid injection device may compare a current filtering time with a previous filtering time.

When a difference between the current filtering time and the previous filtering time is greater than or equal to a first reference value, operation 1151 may be performed. In operation 1151, the medical liquid injection device may increase the evaluation value. Alternatively, when the difference between the current filtering time and the previous filtering time is less than the first reference value, operation 1152 may be performed. In operation 1152, the medical liquid injection device may decrease the evaluation value.

For example, when the current filtering time is set to 2.30 seconds, the previous filtering time is set to 1.90 seconds, and the first reference value is set to 0.30 seconds, the medical liquid injection device may increase the evaluation value by one. The first reference value may be 0.30 seconds, 0.25 seconds, 0.20 seconds, 0.15 seconds, 0.10 seconds, or 0.05 seconds, but the present disclosure is not limited thereto.

Meanwhile, in FIG. 11, it is illustrated that the evaluation value is increased by one in operation 1151, and the evaluation value is decreased by one in operation 1152, but the increased/decreased value of the evaluation value is not limited thereto.

In an embodiment, the magnitude by which the evaluation value is decreased in operation 1152 may be greater than the magnitude by which the evaluation value is increased in operation 1151. For example, in operation 1151, the evaluation value may be increased by one, and in operation 1152 the evaluation value may be decreased by two. That is, the medical liquid injection device may calculate the evaluation value in a way in which a greater decrease weight is given when the difference between the current filtering time and the previous filtering time is less than the first reference value than when the difference therebetween is greater than or equal to the first reference value.

In operation 1160, the medical liquid injection device may compare the evaluation value with a second reference value.

When the evaluation value is greater than or equal to the second reference value, operation 1170 may be performed. In addition, when the evaluation value is less than the second reference value, the method may return to operation 1120. For example, in a case in which the second reference value has “20 operations,” operation 1170 may be performed when the evaluation value has “20 operations or more.” The second reference value may have “10” operations,” “15 operations,” “20 operations,” or “25 operations,” but the present disclosure is not limited thereto.

In operation 1170, the medical liquid injection device may compare the current filtering time with a third reference value.

When the current filtering time is greater than or equal to the third reference value, operation 1180 may be performed. In addition, when the current filtering time is less than the third reference value, the method may return to operation 1120.

In operation 1180, the medical liquid injection device may determine that inlet occlusion occurs.

For example, when the current filtering time is 2.30 seconds and the third reference value is set to 2.25 seconds, the medical liquid injection device may determine that the inlet occlusion occurs.

In various reasons such as various foreign substances, mechanical damage, blood coagulation around a needle, and the like, the occlusion may occur in the inlet that is a passage through which the medical liquid is injected into a user.

Referring to operation 1130, since errors and deviations may occur in the driving time of the pump module whenever calculation is performed, in order to reduce the errors and the deviations, the present disclosure may use the filtering time obtained by filtering a predetermined number of consecutive driving times.

In addition, when operations 1140 to 1170 are taken together, in the present disclosure, the effect of noise may be minimized by determining the occurrence of inlet occlusion of the medical liquid injection device only when both a condition in which the filtering time tends to increase (that is, the evaluation value is greater than or equal to the second reference value) and a condition in which the filtering time is greater than or equal to a predetermined value (that is, the current filtering time is greater than or equal to the third reference value) are satisfied.

Meanwhile, in an embodiment, operation 1170 may be omitted. In this case, when the evaluation value is less than the second reference value in operation 1160, operation 1180 may be performed.

Figure 12:
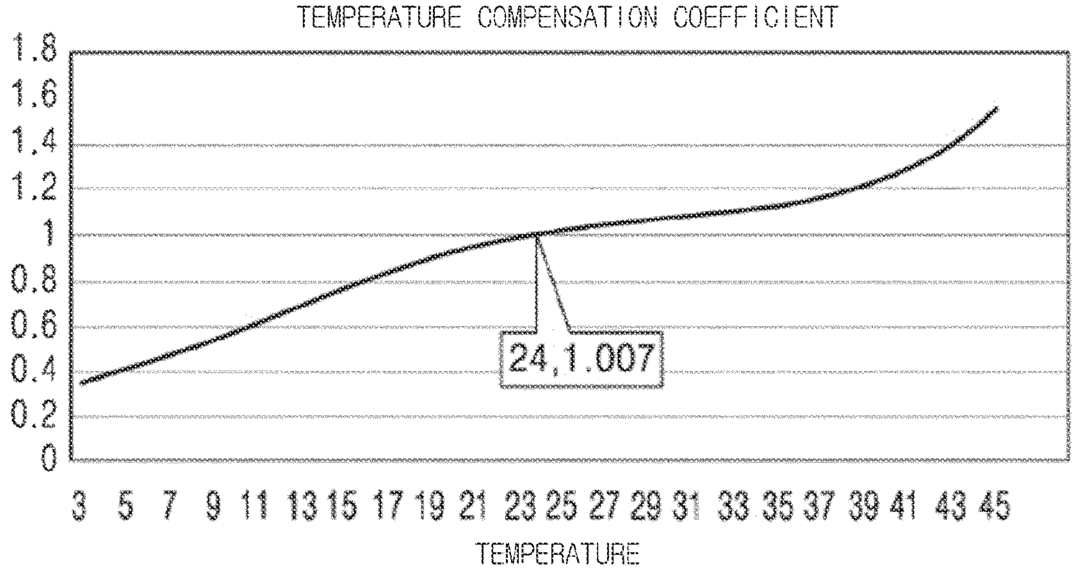
FIG. 12 is a view for describing a temperature compensation coefficient for compensating for the driving time of the pump module according to an embodiment.

FIG. 12 is a view for describing a temperature compensation coefficient for compensating for the driving time of the pump module according to an embodiment.

The medical liquid injection device may further include a temperature detection sensor configured to measure a temperature inside and/or outside the medical liquid injection device. The medical liquid injection device may be used in an environment in which temperature variation is large. For example, the temperature of the medical liquid injection device may vary according to a user’s body temperature and an external environment.

The medical liquid injection device may receive a current temperature of the medical liquid injection device from the temperature detection sensor. The medical liquid injection device may calculate a compensated driving time by comparing the reference temperature and the current temperature and compensating for the driving time.

The medical liquid injection device may calculate a filtering time by filtering a predetermined number of consecutive compensated driving times. Contents of a method of determining the inlet occlusion by using the filtering time by the medical liquid injection device after calculating the filtering time overlap with those described in operations 1140 to 1180 of FIG. 11, and thus will be omitted herein.

When other conditions (e.g., ambient pressure or the like) except for the temperature are the same, the driving time of the pump module may be affected by the temperature. As the current temperature of the medical liquid injection device increases, the driving time of the pump module decreases. In addition, as the current temperature of the medical liquid injection device decreases, the driving time of the pump module increases.

In the present disclosure, the compensated driving time may be used to prevent the medical liquid injection device from erroneously determining that inlet occlusion occurs even when the inlet occlusion does not actually occur, due to a driving-time error due to the temperature.

Referring to FIG. 12, an x-axis represents the temperature, and a y-axis represents the temperature compensation coefficient. As the temperature increases, the value of the temperature compensation coefficient may increase. For example, when the temperature of the medical liquid injection device is 24° C., the temperature compensation coefficient may be 1.007.

The medical liquid injection device may calculate the compensated driving time by multiplying the temperature compensation coefficient by the driving time of the pump module. For example, when the temperature of the medical liquid injection device is 39° C., the temperature compensation coefficient is 1.5, and the driving time of the pump module is 2.0 seconds, the compensated driving time may be 3.0 seconds (=2.0 seconds×1.5).

In an embodiment, the temperature compensation coefficient according to the temperature of the medical liquid injection device may be stored in the form of a lookup table in a memory of the medical liquid injection device. Alternatively, the medical liquid injection device may calculate the temperature compensation coefficient according to a temperature, in real time, through predetermined calculations.

Figure 13:
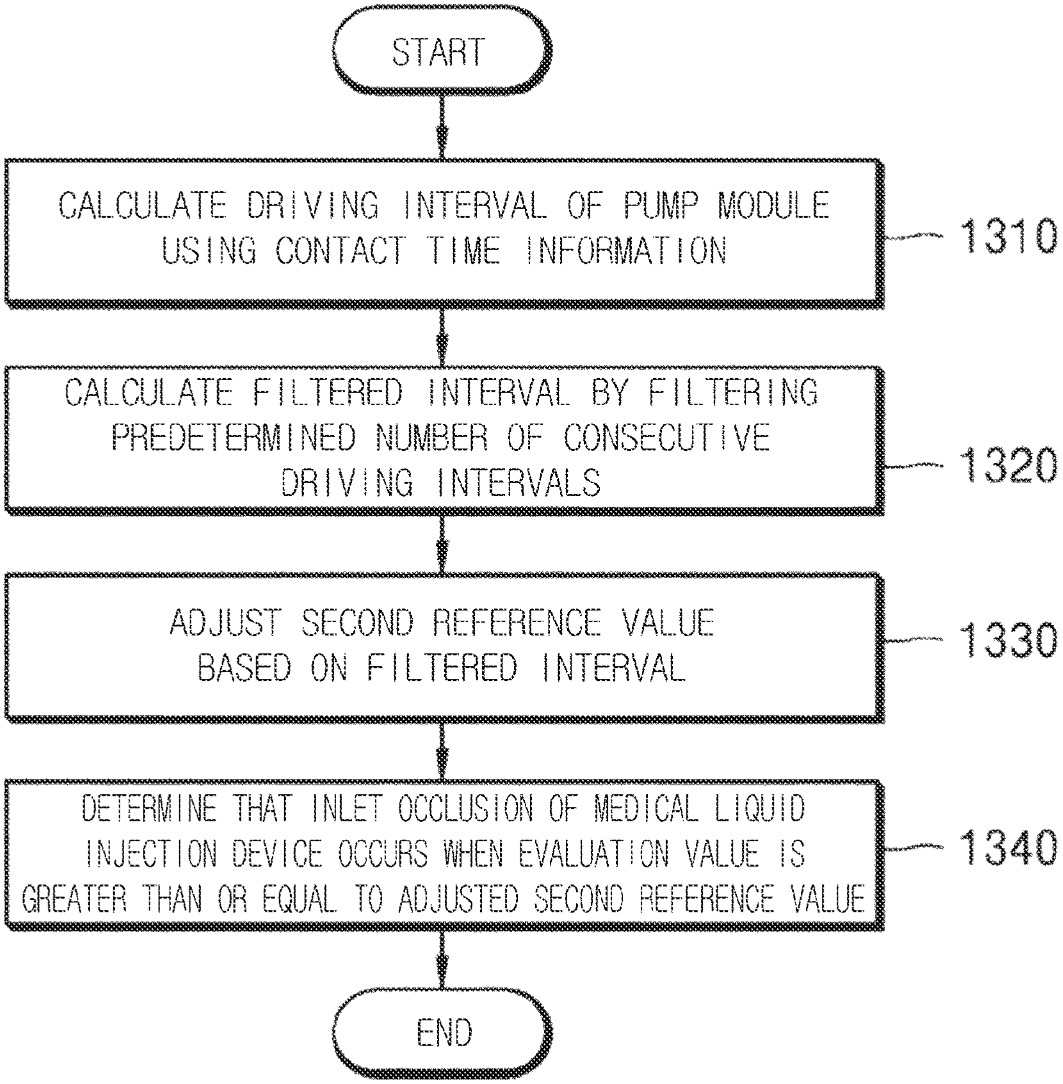
FIG. 13 is a flowchart of a method of determining the occurrence of inlet occlusion of the medical liquid injection device in consideration of a driving interval of the pump module according to an embodiment.

FIG. 13 is a flowchart of a method of determining the occurrence of inlet occlusion of the medical liquid injection device in consideration of a driving interval of the pump module according to an embodiment.

Referring to FIG. 13, in operation 1310, the medical liquid injection device may calculate a driving interval of the pump module using contact time information.

Describing with reference to FIGS. 3 and 9, the processor 800 may obtain first contact time information on a time at which the first end 431 is separated from contact with the second sensor 422, and obtain second contact time information on a time at which the first end 431 comes into contact with the first sensor 421. Thereafter, the processor 800 may calculate a first driving time of the pump module 100 on the basis of the first and second contact time information described above. Here, the first driving time may be a driving time for driving a push operation of the pump module 100.

Similarly, the processor 800 may obtain third contact time information on a time at which the first end 431 is separated from contact with the first sensor 421, and obtain fourth contact time information on a time at which the first end 431 comes into contact with the second sensor 422. Thereafter, the processor 800 may calculate a second driving time of the pump module 100 on the basis of the third and fourth contact time information described above. Here, the second driving time may be a driving time for driving a pull operation of the pump module 100.

In an embodiment, a time until the pump module completes one push operation and one pull operation may be set to the driving time. In addition, a time until a next push operation is started after the pull operation is completed may be set to a driving interval. However, the setting of the driving time and the driving interval as described above is merely an example. For example, a time until the next pull operation is started after the push operation is completed may be set to the driving interval.

In operation 1320, the medical liquid injection device may calculate a filtered interval by filtering a predetermined number of consecutive driving intervals.

For example, the medical liquid injection device may obtain 12 consecutive driving intervals and calculate a filtered interval by applying a moving average method thereto. However, the number of driving intervals and the filtering method used to calculate the filtered interval are not limited to those of the above-described example.

In operation 1330, the medical liquid injection device may adjust a second reference value on the basis of the filtered interval.

Specifically, the medical liquid injection device may adjust the second reference value to be lower as the filtered interval is larger, and adjust the second reference value to be higher as the filtered interval is smaller.

The larger the filtered interval indicates that an injection rate of the medical liquid injection device decreases, and the smaller the filtered interval indicates that the injection rate of the medical liquid injection device increases. In the present disclosure, sensitivity may be applied by adjusting the second reference value according to the filtered interval. In the present disclosure, as the filtered interval increases, that is, the injection rate of the medical liquid injection device decreases, the second reference value may be adjusted to be low in order to more quickly determine whether inlet occlusion occurs.

For example, Equation 1 may be used for a method of adjusting the second reference value.

$$B = \frac{(T_{max} - T)}{T_{max}} \times (B_{max} - B_{min}) + B_{min} \quad \text{[Equation 1]}$$

In Equation 1, B denotes an adjusted second reference value, $B_{max}$ denotes a maximum second reference value, $B_{min}$ denotes a minimum second reference value, T denotes an average filtered interval, and $T_{max}$ denotes a maximum filtered interval. The $T_{max}$, $B_{max}$, and $B_{min}$ are preset values.

In an embodiment, the medical liquid injection device may adjust the second reference value according to an injection type. For example, the injection rate of the medical liquid injection device in a case in which the injection type is “Basal” is slower than that in a case in which the injection type is “Bolus.” The medical liquid injection device may more quickly determine whether the inlet occlusion occurs by adjusting the second reference value in the case in which the injection type is “Basal” to be lower than that in the case in which the injection type is “Bolus.”

In operation 1340, when the evaluation value is greater than or equal to the adjusted second reference value, the medical liquid injection device may determine that the inlet occlusion occurs.

In the present disclosure, it is possible to more accurately determine whether the inlet occlusion occurs by adjusting the detection sensitivity in such a way that the second reference value is set to a smaller value as the injection rate of the medical liquid injection device is decreased and the second reference value is set to a larger value as the injection rate of the medical liquid injection device is increased.

Meanwhile, when the medical liquid is injected by combining various injection types (e.g., Bolus, Extended Bolus, Basal, and the like), a problem arises in that it is difficult to calculate an average of all injection rates. In the present disclosure, the driving interval is measured for each basic unit of injection of the pump module, and the injection rate (e.g., the filtered interval) is calculated on the basis of the measured driving interval, and thus all the injection rates may be easily calculated even when the injection types are combined.

Figure 14:
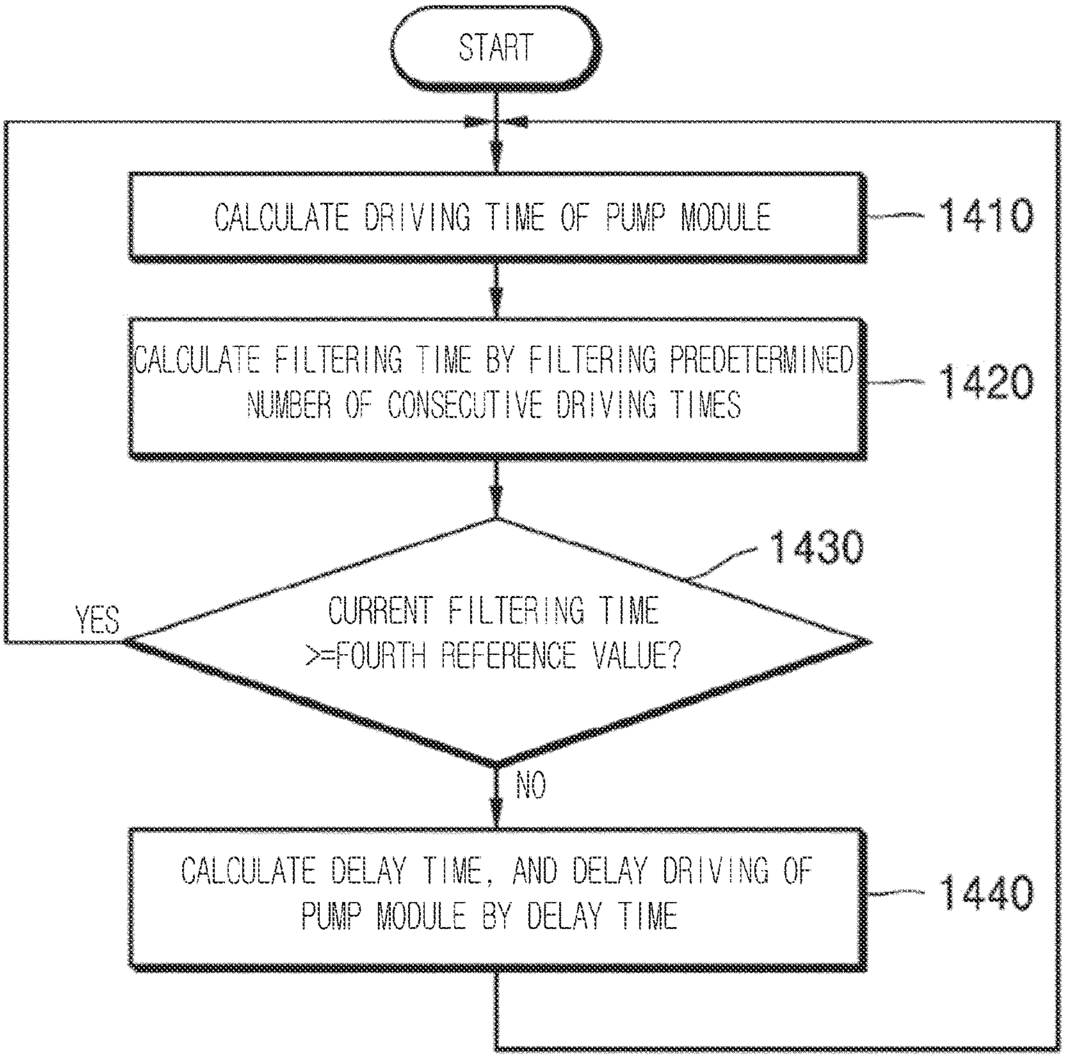
FIG. 14 is a flowchart of a method of delaying the driving of the pump module according to an injection rate according to an embodiment.

FIG. 14 is a flowchart of a method of delaying the driving of the pump module according to the injection rate according to an embodiment.

When an injection amount in the medical liquid injection device is instantaneously large, that is, when the injection rate of the medical device is high, the internal pressure of the medical liquid injection device may be increased even in a normal situation in which the inlet is not occluded. In addition, even when the inlet is not occluded, the internal pressure of the medical liquid injection device may be instantaneously increased by a person’s absorption rate, skin, an attachment site, blood, a needle state, a temperature, an atmospheric pressure, exercise, compression, impact, and the like.

The medical liquid injection device may delay the driving of the pump module in order to prevent a case in which an instantaneous increase in the internal pressure of the medical liquid injection device is erroneously determined as the occurrence of the inlet occlusion.

Referring to FIG. 14, in operation 1410, the medical liquid injection device may calculate a driving time of the pump module.

In operation 1420, the medical liquid injection device may calculate a filtering time by filtering a predetermined number of consecutive driving times.

Operations 1410 and 1420 are the same as operations 1120 and 1130 of FIG. 10, respectively, and thus detailed descriptions thereof will be omitted.

In operation 1430, the medical liquid injection device may compare a current filtering time with a fourth reference value.

When the current filtering time is less than the fourth reference value, operation 1440 may be performed. Alternatively, when the current filtering time is greater than or equal to the fourth reference value, the method may return to operation 1410.

Describing with reference to FIG. 10, the fourth reference value may be less than the third reference value. For example, when an average driving time (or average filtering time) of the pump module is 2.0 seconds, since the third reference value is a time that is a criterion for determining whether inlet occlusion occurs, the third reference value may be set to 6.0 seconds, which is greater than the average driving time, and the fourth reference value may be set to 4.0 seconds, which is less than the third reference value, in order to reduce erroneous determination of the inlet occlusion due to factors such as transient noise or pressure rise before determining the inlet occlusion.

In operation 1440, the medical liquid injection device may calculate a delay time, and delay the driving of the pump module by the delay time.

In an embodiment, the medical liquid injection device may calculate the delay time to be proportional to the filtering time. The delay time may have a value between a predetermined maximum delay time and a predetermined minimum delay time. The delay time may be calculated by multiplying the filtering time by a predetermined proportional constant.

Figure 15:
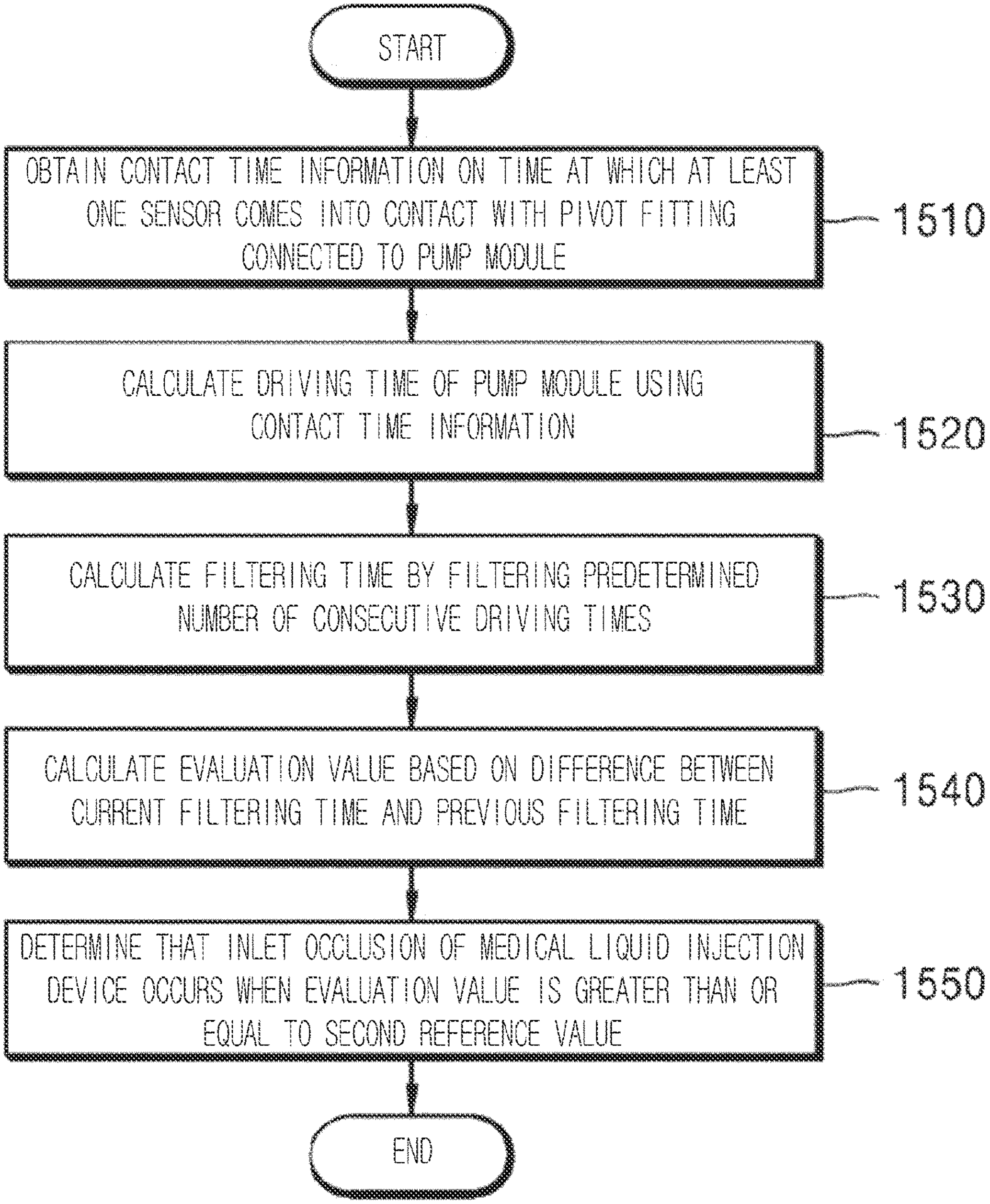
FIG. 15 is a flowchart illustrating a method of determining the occurrence of inlet occlusion of the medical liquid injection device according to an embodiment.

FIG. 15 is a flowchart illustrating a method of determining the occurrence of inlet occlusion of the medical liquid injection device according to an embodiment.

Referring to FIG. 15, in operation 1510, the processor may obtain contact time information on a time at which at least one sensor comes into contact with the pivot fitting connected to the pump module.

Describing with reference to FIGS. 3 and 9, the processor 800 may obtain first contact time information on a time at which the first end 431 is separated from contact with the second sensor 422, and obtain second contact time information on a time at which the first end 431 comes into contact with the first sensor 421.

Similarly, the processor 800 may obtain third contact time information on a time at which the first end 431 is separated from contact with the first sensor 421, and obtain fourth contact time information on a time at which the first end 431 comes into contact with the second sensor 422.

In operation 1520, the processor may calculate a driving time of the pump module using the contact time information.

Describing with reference to FIGS. 3 and 9, the processor 800 may calculate a first driving time of the pump module 100 on the basis of the first and second contact time information. Here, the first driving time may be a driving time for driving a push operation of the pump module 100.

In addition, the processor 800 may calculate a second driving time of the pump module 100 on the basis of the third and fourth contact time information described above. Here, the second driving time may be a driving time for driving a pull operation of the pump module 100.

In operation 1530, the processor may calculate a filtering time by filtering a predetermined number of consecutive driving times.

The processor may use the first driving time or the second driving time to calculate the filtering time. Alternatively, the processor may use a time obtained by adding the first driving time and the second driving time to calculate the filtering time.

For example, the processor may obtain 12 consecutive driving times and calculate the filtering time by applying a moving average method thereto. However, the number of the driving times and the filtering method used to calculate the filtering time are not limited to those in the above-described example.

In operation 1540, the processor may calculate an evaluation value on the basis of a difference between a current filtering time and a previous filtering time. The evaluation value may be set to an initial set value. For example, the initial set value may be zero, and the evaluation value may be maintained at a value greater than or equal to zero, When the difference between the current filtering time and the previous filtering time is greater than or equal to the first reference value, the processor may increase the evaluation value. Alternatively, when the difference between the current filtering time and the previous filtering time is less than the first reference value, the processor may decrease the evaluation value.

In operation 1550, when the evaluation value is greater than or equal to the second reference value, the processor may determine that inlet occlusion of the medical liquid injection device occurs.

For example, in a case in which the second reference value is "20 operations," when the evaluation value is greater than or equal to "20 operations," the processor may determine that the inlet occlusion of the medical liquid injection device occurs. The second reference value may have "10" operations," "15 operations," "20 operations," or "25 operations," but the present disclosure is not limited thereto.

Various embodiments of the present disclosure may be implemented as software (e.g., a program) including one or more instructions that are stored in a storage medium that is readable by a machine. For example, a processor of the machine may invoke at least one of the one or more instructions stored in the storage medium, and execute the at least one instruction. This allows the machine to be operated to perform at least one function according to the at least one instruction invoked. The one or more instructions may include a code generated or executed by a compiler or an interpreter. The machine-readable storage medium may be provided in the form of a non-transitory storage medium. Here, the term "non-transitory" only means that the storage medium is a tangible device, and does not include a signal (e.g., an electromagnetic wave), but this term does not differentiate between a case in which data is semi-permanently stored in the storage medium and a case in which the data is temporarily stored in the storage medium.

According to an embodiment, the methods according to various embodiments may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. When distributed online, at least a portion of the computer program product may be temporarily generated or at least temporarily stored in the machine-readable storage medium, such as a memory of the manufacturer's server, a server of the application store, or a relay server.

In addition, in the present specification, a "part" may be a hardware component such as a processor or a circuit, and/or a software component executed by a hardware component such as a processor.

The scope of the present embodiment will be defined by the following claims rather than the above-detailed description, and all changes and modifications derived from the meaning and the scope of the claims and equivalents thereof should be understood as being included in the scope of the present embodiment.

The invention claimed is:

1. A medical liquid injection device comprising:

a pump module including a shaft configured to perform a linear reciprocating movement along one direction;

a pivot fitting including a first end connected to the shaft and a second end configured to perform a rotational reciprocating movement by the linear reciprocating movement between a first rotational position and a second rotational position;

at least one sensor configured to obtain contact time information on a time at which the at least one sensor comes into contact with the second end at one of the first rotational position or the second rotational position; and a processor configured to calculate a driving time of the pump module using the contact time information, and determine an occurrence of an inlet occlusion of the medical liquid injection device on a basis of the driving time.

2. The medical liquid injection device of claim 1, wherein the processor calculates a filtering time by filtering a predetermined number of consecutive driving times, calculates an evaluation value in such a manner that when a difference between a current filtering time and a previous filtering time is greater than or equal to a first reference value, the evaluation value is increased, and when the difference between the current filtering time and the previous filtering time is less than the first reference value, the evaluation value is decreased, and determines that the inlet occlusion of the medical liquid injection device has occurred when the evaluation value is greater than or equal to a second reference value.

3. The medical liquid injection device of claim 2, wherein the processor determines that the inlet occlusion of the medical liquid injection device has occurred when the evaluation value is greater than or equal to the second reference value and the current filtering time is greater than or equal to a third reference value.

4. The medical liquid injection device of claim 3, wherein the processor delays driving of the pump module when the current filtering time is less than a fourth reference value, and the fourth reference value is less than the third reference value.

5. The medical liquid injection device of claim 2, wherein the medical liquid injection device further comprises a temperature detection sensor configured to measure a temperature of the medical liquid injection device, the processor receives a current temperature from the temperature detection sensor, calculates a compensated driving time by compensating for the driving time on a basis of the current temperature, and calculates the filtering time by filtering a predetermined number of consecutive compensated driving times.

6. The medical liquid injection device of claim 2, wherein the processor calculates a driving interval of the pump module using the contact time information, calculates a filtered interval by filtering a predetermined number of consecutive driving intervals, adjusts the second reference value on the basis of the filtered interval, and determines that the inlet occlusion of the medical liquid injection device has occurred when the evaluation value is greater than or equal to the adjusted second reference value.

7. A method of determining an occurrence of an inlet occlusion of a medical liquid injection device, the method comprising:

obtaining contact time information on a time at which at least one sensor comes into contact with a pivot fitting connected to a pump module, wherein the pivot fitting performs a rotational reciprocating movement between the at least one sensor and a rotational position;

calculating a driving time of the pump module using the contact time information; and determining the occurrence of the inlet occlusion of the medical liquid injection device on a basis of the driving time, wherein the determining of the occurrence of the inlet occlusion of the medical liquid injection device includes:

calculating a filtering time by filtering a predetermined number of consecutive driving times;

calculating an evaluation value in such a manner that when a difference between a current filtering time and a previous filtering time is greater than or equal to a first reference value, the evaluation value is increased, and when the difference between the current filtering time and the previous filtering time is less than the first reference value, the evaluation value is decreased, and determining that the inlet occlusion of the medical liquid injection device has occurred when the evaluation value is greater than or equal to a second reference value.

8. A computer program product comprising one or more non-transitory computer-readable media storing a program for implementing a method including:

obtaining contact time information on a time at which at least one sensor comes into contact with a pivot fitting connected to a pump module, wherein the pivot fitting performs a rotational reciprocating movement between the at least one sensor and a rotational position;

calculating a driving time of the pump module using the contact time information; and determining an occurrence of an inlet occlusion of a medical liquid injection device on a basis of the driving time;

wherein the determining of the occurrence of the inlet occlusion of the medical liquid injection device includes;

calculating a filtering time by filtering a predetermined number of consecutive driving times;

calculating an evaluation value in such a manner that when a difference between a current filtering time and a previous filtering time is greater than or equal to a first reference value, the evaluation value is increased, and when the difference between the current filtering time and the previous filtering time is less than the first reference value, the evaluation value is decreased, and determining that the inlet occlusion of the medical liquid injection device has occurred when the evaluation value is greater than or equal to a second reference value.

* * * * *